(12) United States Patent
Ishihara

(10) Patent No.: US 9,650,411 B2
(45) Date of Patent: May 16, 2017

(54) METHOD OF PURIFYING PROTEIN

(71) Applicant: KYOWA HAKKO KIRIN CO., LTD, Tokyo (JP)

(72) Inventor: Takashi Ishihara, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 151 days.

(21) Appl. No.: 13/826,195

(22) Filed: Mar. 14, 2013

(65) Prior Publication Data

US 2014/0046038 A1    Feb. 13, 2014

Related U.S. Application Data

(60) Provisional application No. 61/680,433, filed on Aug. 7, 2012.

(51) Int. Cl.
| | | |
|---|---|---|
| C07K 1/18 | (2006.01) | |
| C07K 16/00 | (2006.01) | |
| C07K 1/22 | (2006.01) | |
| C07K 16/06 | (2006.01) | |
| C07K 1/30 | (2006.01) | |

(52) U.S. Cl.
CPC .............. *C07K 1/18* (2013.01); *C07K 1/22* (2013.01); *C07K 16/00* (2013.01); *C07K 16/065* (2013.01)

(58) Field of Classification Search
None
See application file for complete search history.

(56) References Cited

U.S. PATENT DOCUMENTS

| | | | |
|---|---|---|---|
| 4,902,783 A | 2/1990 | Goda et al. | |
| 5,219,999 A | 6/1993 | Suzuki et al. | |
| 5,294,699 A | 3/1994 | Ohmura et al. | |
| 5,644,036 A | 7/1997 | Ramage et al. | |
| 2002/0056686 A1* | 5/2002 | Kyrlidis et al. | ............ 210/656 |
| 2008/0026041 A1* | 1/2008 | Tepper et al. | ................ 424/445 |
| 2008/0286838 A1* | 11/2008 | Yuan et al. | .................... 435/101 |
| 2011/0139717 A1 | 6/2011 | Malenfant et al. | |
| 2013/0197200 A1* | 8/2013 | Bian et al. | ................. 530/388.1 |
| 2013/0203969 A1* | 8/2013 | Jaber | ..................... C07K 16/00 530/388.1 |

FOREIGN PATENT DOCUMENTS

| | | |
|---|---|---|
| EP | 0180766 A2 | 5/1986 |
| EP | 1577319 A1 * | 9/2005 |
| JP | 63-000297 A | 1/1988 |
| JP | 3-271234 A | 12/1991 |
| JP | 4-054198 A | 2/1992 |
| JP | 5-504579 A | 7/1993 |
| WO | 92/07084 A1 | 4/1992 |
| WO | 2009/009523 A2 | 1/2009 |
| WO | 2009/063647 A1 | 5/2009 |
| WO | 2011/081898 A1 | 7/2011 |
| WO | 2013/028330 A2 | 2/2013 |

OTHER PUBLICATIONS

International Search Report for PCT/JP2013/057902 dated Jun. 4, 2013 [PCT/ISA/210].
Chen, "Removal of Fatty Acids from Serum Albumin by Charcoal Treatment", The Journal of Biological Chemistry, vol. 242, No. 2, Jan. 1967, XP 002395537, 9 pages total.
Search Report dated Feb. 8, 2016, issued by the European Patent Office in counterpart European Application No. 13828251.2.

\* cited by examiner

*Primary Examiner* — Daniel E Kolker
*Assistant Examiner* — James Rogers
(74) *Attorney, Agent, or Firm* — Sughrue Mion, PLLC

(57) ABSTRACT

The present invention relates to a method for purifying a protein by separating the protein from impurities in a non-adsorption mode using an activated carbon. In particular, the present invention relates to a method for purifying an antibody using the activated carbon instead of protein A affinity chromatography.

16 Claims, 22 Drawing Sheets

METHOD OF PURIFYING PROTEIN

TECHNICAL FIELD

The present invention relates to a method for purifying a protein and a method for preparing a protein comprising the purification method. In particular, the present invention relates to a method for purifying an antibody and a method for preparing an antibody comprising the purification method.

BACKGROUND ART

Development of genetic recombination technologies has provided drugs including a variety of proteins as an active ingredient. In particular, numerous drugs including antibodies as an active ingredient have been recently developed and commercialized. In addition, efficient production of these proteins in large-scale has become a more important issue in biopharmaceutical industry.

Generally, such proteins are produced by culturing recombinant cells in which a vector including a gene encoding a protein of interest is inserted. The culture broth includes impurities such as a wide variety of medium-derived components, host cell-derived components, protein-derived by-products or the like, in addition to the protein of interest. Thus, it is a very difficult and challenging task to achieve both the purification of the protein of interest by removing impurities to meet purity requirements for protein drugs as well as the efficient production of the protein of interest in large-scale.

In general, the protein purification method is carried out by a combination of different modes of chromatography. Chromatography is to separate the protein of interest from impurities, for example, based on charge, hydrophilicity, molecular size or the like.

In particular, when the protein of interest is an antibody, Protein A affinity chromatography or Protein G affinity chromatography is used as one of chromatography for purifying the antibody, by using binding property of Protein A or Protein G to the specific region of antibody such as Fc chain (Patent Document 1).

However, Protein A affinity supports generally used are very expensive in comparison to ion exchange supports or hydrophobic supports, and a vast amount of supports are needed for large-scale purification of antibodies in industrial drug productions or the like, resulting in an inevitable increase in the production costs.

Further, protein A affinity chromatography or protein G affinity chromatography is generally carried out in an adsorption mode of specifically adsorbing the antibody of interest onto the support, washing the adsorbing support to separate impurities, and finally eluting the antibody of interest from the support. In this regard, buffers used in the washing and eluting steps are different from each other, scale-up of chromatography apparatus brings out enlargement or complexity of the accompanying production facilities such as buffer tank, and moreover, manipulations become complicated. All of these factors are the cause of increasing production costs.

For these reasons, the drugs including proteins as an active ingredient require much higher production costs than drugs including small-molecule compounds as an active ingredient, which is a challenging problem. In other words, a reduction in the protein purification cost is demanded in this field.

On the other hand, it is known that enzymes secreted from host cells are included in a culture broth containing the protein of interest, and the protein of interest is degraded, modified, oxidized, or reduced by these enzymes during the protein purification process. For this reason, addition of enzyme inhibitors during the protein purification has been considered to prevent degradation, modification, oxidation, or reduction of the protein of interest (Patent Document 2). However, when the enzyme inhibitors are used during the protein purification, an additional process of removing the inhibitors is required, and moreover, certain inhibitors may affect the quality of the purified protein. Therefore, it cannot be said that the addition of inhibitors is the best way. Removal of host cell-derived enzymes is considered as one of the drastic methods to solve the problems, but it is essential to use chromatography. There is no simple method of removing these enzymes.

Activated carbon is an inexpensive natural material having extensive non-specific adsorption properties, and used as an adsorbent or as a decolorant in the industrial fields, such as the production of chemicals and foods, sewage or waste water treatment, water filtration, and production of small-molecule drugs. However, due to the extensive non-specific adsorption properties, it has been thought that there are difficulties in the use of activated carbon for high performance protein purification such as separation of the above-mentioned impurities. Thus, a method of purifying a protein using the activated carbon has not been known yet.

CITATION LIST

Patent Documents

[Patent Document 1] Japanese Patent Publication No. Hei5-504579
[Patent Application 2] International Patent Publication No. 2009/009523

SUMMARY OF THE INVENTION

Problems to be Solved by the Invention

An object of the present invention is to provide a purification method which can lower production cost or reduce labor than the conventional protein purification methods, and has impurity separation properties higher than or equivalent to the conventional protein purification methods, in particular, as an alternative to protein A affinity chromatography for antibody purification, and a method for preparing a protein comprising the purification method.

Means for Solving the Problems

The present inventors have made many efforts to solve the above objects. As a result, they surprisingly found a method for purifying a protein by separating the protein from impurities using an inexpensive activated carbon in a non-absorption mode, in particular, a method for purifying an antibody using the activated carbon instead of protein A affinity chromatography, thereby completing the present invention.

The present invention relates the following (1) to (14)

(1) A method for purifying a protein, wherein the protein is separated from impurities using an activated carbon to obtain the protein with a low content of impurities.

(2) The purification method described in (1), wherein the protein has a molecular weight of 30000 or more.

(3) The purification method described in (1) or (2), wherein the protein is a glycoprotein.

(4) The purification method described in (3), wherein the glycoprotein is an antibody.

(5) The purification method described in any one of (1) to (4), wherein the protein is a genetically modified protein.

(6) The purification method described in any one of (1) to (5), wherein the impurities are any one of host cell proteins, protein-derived polymers, protein-derived degradation products, or DNAs.

(7) The purification method described in any one of (1) to (6), wherein the method is carried out in a non-adsorption mode.

(8) The purification method described in any one of (1) to (7), wherein the separation is carried out at pH 3 to 8.

(9) The purification method described in any one of (1) to (8), wherein the activated carbon is an activated carbon from wood.

(10) The purification method described in any one of (1) to (9), wherein the activated carbon has an average micropore diameter of 0.5 to 5 nm.

(11) A method for preparing a protein, comprising the purification method of any one of (1) to (10).

(12) The preparation method described in (11), wherein protein A chromatography is not used.

(13) The preparation method described in (11) or (12), comprising any one of anion exchange chromatography, cation exchange chromatography, hydrophobic interaction chromatography, and multimodal chromatography.

(14) The preparation method described in any one of (11) to (13), comprising at least one adsorption-mode chromatography.

(15) A protein that is prepared by the method of any one of (11) to (14).

Effect of the Invention

The present invention provides a purification method which can lower production cost or reduce labor than the conventional protein purification methods, and has impurity separation properties higher than or equivalent to the conventional protein purification methods, in particular, as an alternative to protein A affinity chromatography for antibody purification, and a method for preparing a protein comprising the purification method. The protein prepared by the present invention is useful as a drug.

EMBODIMENTS FOR CARRYING OUT THE INVENTION

Figure 1:
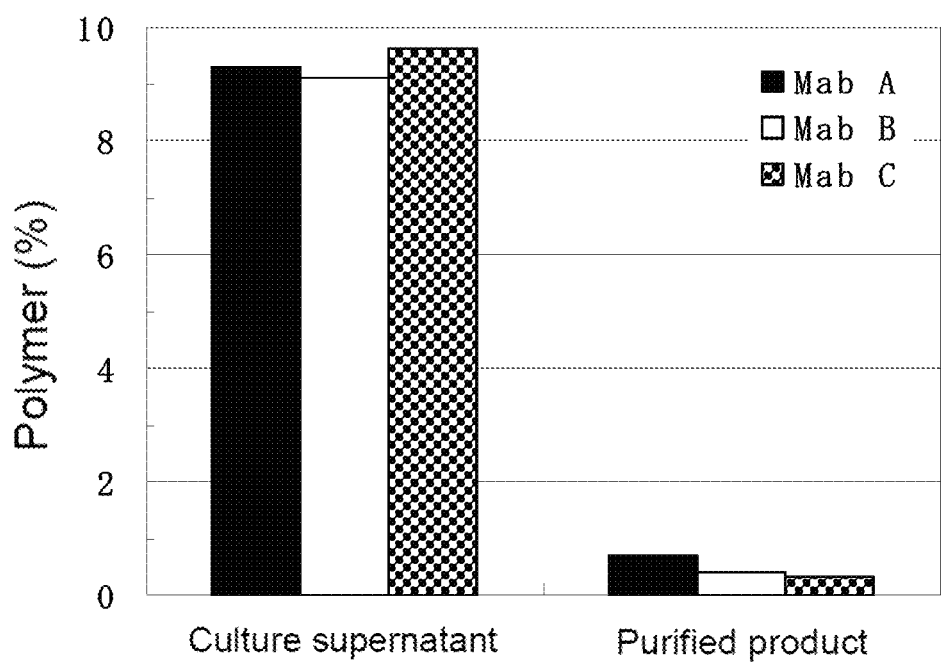
FIG. 1 shows the polymer contents of the supernatant and the final purified product in non-adsorption mode comprising activated carbon purification of Mab A, Mab B and Mab C. The vertical axis represents the polymer content (%), the black color represents Mab A, and the white color represents Mab B, the grey color represents Mab C. From left, the polymer contents of the culture supernatant (Culture supernatant) and the final purified product (Purified product) are represented.

The present invention relates to a method for purifying a protein, in which the protein is separated from impurities using an activated carbon to obtain a protein having a lower content of impurities.

In the present invention, examples of the protein may include natural or non-natural proteins having no sugar chain, natural or non-natural glycoproteins, derivatives thereof or the like. The glycoproteins or derivatives thereof may be compositions comprising molecules different in their sugar chains.

The protein may be a protein having a molecular weight of preferably 30000 or higher, and more preferably 50000 or higher.

Specific examples thereof may include erythropoietin, darbepoetin, antithrombin (α or β form, or mixtures thereof), interferons, interleukins, protein S, tissue plasminogen activator, factor VII, factor VIII, factor IX, thrombomodulin, glucocerebrosidase, α-galactosidase, α-L-iduronidase, acidic α-glucosidase, Granulocyte Colony Stimulating Factor (G-CSF), Granulocyte Macrophage-Colony Stimulating Factor (GM-CSF), thrombopoietin or Megakaryocyte Growth and Development Factor (MGDF), fibroblast growth factor (FGF), epidermal growth factor (EGF), insulin-like growth factor (IGF), brain-derived neurotrophic factor (BDNF), ciliary neurotrophic factor (CTNF), Glial-Cell Derived Neurotrophic Factor (GDNF), or antibodies and, derivatives thereof, or the like, preferably antibodies, and more preferably monoclonal antibodies.

Examples of the antibodies may include mouse antibodies, llama antibodies, chimeric antibodies, humanized antibodies, human antibodies, antibodies with modified Fc regions or the like. Examples of the molecular type may include IgG, IgM, IgA, IgD, IgE, Fab, Fc, Fc-fusion proteins, VH, VL, VHH, Fab'$_2$, scFv, scFab, scDb, scDbFc or the like.

In the purification method of the present invention, a protein-containing aqueous solution that includes a protein of interest and impurities is provided.

Examples of the protein-containing aqueous solution may include a composition obtained from the living body, such as plasma, serum, breast milk, or urine, a culture broth of protein-producing cells or bacteria such as *E. coli*, which are obtained by a genetic recombination technique or a cell fusion technique, a composition obtained from transgenic non-human animals, plants or insects, a composition obtained by cell-free protein synthesis, or the like.

Examples of the protein-producing cell may include a transformed cell in which a gene encoding a protein of interest is integrated in a host cell, or the like.

Examples of the host cell may include cell lines of animal cells, plant cells, yeast cells or the like.

Specific examples thereof may include Chinese hamster ovary cells (CHO cells), mouse myeloma cells such as NS0 cell and SP2/0 cell, rat myeloma cells such as YB2/0 cell and IR983F cell, Syrian hamster kidney-derived BHK cells, human myeloma cells such as Namalwa cell, embryo-stem cells, amphicytula or the like.

A medium for culturing the protein-producing cells may be any medium, as long as it is suitable for culturing each of the cells, and examples of the medium for culturing animal cells may include typical media used for culturing animal cells. For example, any medium of a serum-containing medium, a medium containing no animal-derived component such as serum albumin or serum fraction, a serum-free medium or a protein-free medium may be used, and preferably, the serum-free medium or the protein-free medium is used.

Specifically, for example, RPMI1640 medium [The Journal of the American Medical Association, 199, 519 (1967)], Eagle MEM medium [Science, 122, 501 (1952)], Dulbecco's modified MEM (DMEM) medium [Virology, 8, 396 (1959)], 199 medium [Proceeding of the Society for the Biological Medicine, 73, 1 (1950)], F12 medium [Proc. Natl. Acad. Sci. USA, 53, 288 (1965)], Iscove's Modified Dulbecco medium (IMDM medium) [J. Experimental Medicine, 147, 923 (1978)], EX-CELL302 medium, EX-CELL-CD-CHO medium, and EX-CELL 325 medium (which are manufactured by SAFC bioscience Inc.), CD-CHO medium and CD DG44 medium (which are manufactured by Invitrogen Corp.) or IS CD-CHO medium (manufactured by Irvine Scientific Sales Co., Inc.), modified media thereof, mixed media thereof, concentrated media thereof or the like is used, and preferably RPMI1640 medium, DMEM medium, F12 medium, IMDM medium, EX-CELL302 medium, CD-CHO medium, or IS CD-CHO medium is used.

If necessary, physiologically active substances or nutrient factors essential for growth of the protein-producing cells may be added. These additives may be previously included in the medium prior to cultivation, or further properly supplied to the culture liquid as an additive medium or an additive solution during cultivation. The further supplying method may be carried out using any form of one solution or mixtures of two or more solutions by any of continuous or intermittent supply.

The protein-producing transgenic non-human animals, plants or insects may be non-human animals, plants or insects in which the protein-encoding gene is integrated into their cells. Examples of the non-human animals may include mouse, rat, guinea pig, hamster, rabbit, dog, sheep, pig, goat, cattle or monkey. Examples of the plants may include tobacco, potato, tomato, carrot, soybean, *brassica*, alfalfa, rice, wheat, barley, corn or the like.

Examples of the method for producing the protein-containing aqueous solution may include those described in International Patent Publication No. 2008/120801, Japanese Publication No. Hei3-198792, International Patent Publication No. 2010/018847, International Patent Publication No. 2007/062245, International Patent Publication No. 2007/114496 or the like.

Further, in the present invention, the protein-containing aqueous solution includes a protein-containing aqueous solution obtained from the purification process, in addition to those obtained from the living body, such as plasma, urine or the like. Specific examples thereof may include a cell-free liquid, a precipitate-free liquid, an alcohol fraction, a salting-out fraction, a chromatography eluate or the like.

The cell-free liquid may be a liquid that is prepared by removing cells from the protein-containing aqueous solution obtained from the living body, such as plasma, serum, breast milk, or urine, the protein-containing aqueous solution obtained from transgenic non-human animals, plants or insects, the protein-containing aqueous solution obtained from cells established by the genetic recombination technique, the protein-containing aqueous solution obtained from the purification process, or the like. Specific examples thereof may include solutions that are obtained by removing cells from a cell culture broth by centrifugation, cross-flow filtration (Tangential flow filtration), filtration using a depth filter, filtration using a membrane filter, dialysis, combinations thereof or the like.

Specific examples of the depth filter may include a Millistak+ HC depth filter, a Millistak+ DE depth filter, a Millistak+ CE depth filter (manufactured by Merck millipore Corp.), a SUPRA P depth filter (manufactured by Pall Corp.), a Sartoclear PB depth filter, a Sartoclear PC depth filter (manufactured by Sartorius Corp.), a Zeta plus SP depth filter, a Zeta plus AP depth filter, a Zeta plus LA depth filter, a Zeta plus-Delipid depth filter, a Zeta plus ZA depth filter or a Zeta plus EXT charged depth filter (manufactured by Sumitomo 3M Ltd., but are not limited thereto.

The precipitate-free liquid may be a liquid that is prepared by performing flocculation or two-phase separation of the protein-containing aqueous solution obtained from the living body, such as plasma, serum, breast milk, or urine, the protein-containing aqueous solution obtained from transgenic non-human animals, plants or insects, the protein-containing aqueous solution obtained from cells established by the genetic recombination technique, the protein-containing aqueous solution obtained by cell-free protein synthesis or the protein-containing aqueous solution obtained from the purification process by low-pH treatment or by addition of caprylic acid, an organic solvent, polyethylene glycol, a surfactant, a salt, an amino acid, a polymer or the like, and then by removing precipitates therefrom. Examples of the method for removing precipitates may include centrifugation, cross-flow filtration (Tangential flow filtration), filtration using a depth filter, filtration using a membrane filter, dialysis, combinations thereof or the like.

The pH of the low-pH treatment is preferably pH 3 to 6, and adjusted by addition of an acid such as hydrochloric acid, acetic acid, citric acid, phosphoric acid or the like.

The alcohol fraction may be a fraction that is prepared by adding alcohol or the like to the protein-containing aqueous solution obtained from the living body, such as plasma, serum, breast milk, or urine, the protein-containing aqueous solution obtained from transgenic non-human animals, plants or insects, the protein-containing aqueous solution obtained from cells established by the genetic recombination technique, the protein-containing aqueous solution obtained by cell-free protein synthesis or the protein-containing aqueous solution obtained from the purification process. Specific examples thereof may include fractions obtained by low temperature ethanol fraction or the like.

The salting-out fraction may be a fraction that is prepared by adding a salt such as ammonium sulfate, sodium sulfate, sodium citrate, sodium chloride, potassium chloride or the like to the protein-containing aqueous solution obtained from the living body, such as plasma, serum, breast milk, or urine, the protein-containing aqueous solution obtained from transgenic non-human animals, plants or insects, the protein-containing aqueous solution obtained from cells established by the genetic recombination technique, the protein-containing aqueous solution obtained by cell-free protein synthesis or the protein-containing aqueous solution obtained from the purification process, so as to precipitate proteins.

The chromatography eluate may be a protein eluate that is prepared by adsorbing the protein-containing aqueous solution obtained from the living body, such as plasma, serum, breast milk, or urine, the protein-containing aqueous solution obtained from transgenic non-human animals, plants or insects, the protein-containing aqueous solution obtained from cells established by the genetic recombination technique, the protein-containing aqueous solution obtained by cell-free protein synthesis or the protein-containing aqueous solution obtained from the purification process onto a support or a membrane used in the chromatography so as to elute it using a proper elution solution, or by non-adsorbing it.

The support or the membrane used in the chromatography may include an affinity support, an ion exchange support, an ion exchange membrane, a gel filtration support, a hydrophobic interaction support, a reverse phase support, a hydroxyapatite support, a fluoroapatite support, a cellulose sulfate support, an agarose sulfate support, a multimodal support or the like.

The ion exchange support or the ion exchange membrane may be a support or a membrane that is prepared by directly or indirectly immobilizing a molecule having an ion exchange group, such as a sulfate group, a methyl sulfate group, a sulfophenyl group, a sulfonpropyl group, a carboxymethyl group, a quaternary ammonium group, a quaternary aminoethyl group, a diethylaminoethyl group or the like onto a base support or a membrane, for example, a polymer or a derivative thereof (including crosslinked polymer) such as cellulose, sepharose, agarose, chitosan, an acrylic acid polymer or a styrene-divinyl benzene copolymer, a polymer consisting of silica particles, glass particles, ceramic particles, or surface-treated particles thereof. Specific examples thereof may include Q Sepharose XL, Q Sepharose FF, DEAE Sepharose FF, ANX Sepharose FF, Capto Q, Capto DEAE, Capto Q ImpRes (which are manufactured by GE Healthcare Ltd., Inc.), TOYOPEARL GigaCap Q-650, TOYOPEARL SuperQ-650 (which are manufactured by TOSOH Corp.), Fractogel DEAE, Fractogel TMAE, Fractogel TMAE Hicap, Eshmuno Q (which are manufactured by Merck millipore Corp.), Cellufine MAX-Q (manufactured by JNC Corp.), Mustang Q (manufactured by Pall Corp.), Sartobind Q, Sartobind STIC (which are manufactured by Sartorius Corp.), SP Sepharose FF, CM Sepharose FF, SP Sepharose XL, Capto S (which are manufactured by GE Healthcare Ltd., Inc.), Poros 50 HS, Poros 50 XS (which are manufactured by Applied Biosystems Inc.), Eshmuno S, Fractogel COO$^-$, Fractogel SO$^{3-}$, Fractogel SE Hicap (which are manufactured by Merck millipore Corp.), TOYOPEARL GigaCap S-650, TOYOPEARL GigaCap CM-650 (which are manufactured by TOSOH Corp.), Cellufine MAX-S (manufactured by JNC Corp.), Mustang S (manufactured by Pall Corp.) or Sartobind S (manufactured by Sartorius Corp.), DIAION PK, DIAION PA, DIAION CR, DIAION CR, DIAION AMP (which are manufactured by Mitsubishi Chemical Corp.) or the like, but are not limited thereto.

The affinity support may be a support that is prepared by directly or indirectly immobilizing a molecule having an affinity for the protein of interest, for example, heparin, protein A, protein G protein L or the like, onto the above base support, and specific examples thereof may include Heparin Sepharose 6 Fast Flow (manufactured by GE Healthcare Ltd., Inc.), Procep-heparin (manufactured by Merck millipore Corp.), TOYOPEARL AF-Heparin-650 (manufactured by TOSOH Corp.), Heparin HyperD (manufactured by Pall Corp.), MabSelect, Protein A Sepharose FF, MabSelect Xtra, MabSelect SuRe, MabSelect SuRe LX, Protein G Sepharose FF, Capto L (which are manufactured by GE Healthcare Ltd., Inc.), Prosep vA Hicapacity, Prosep vA Ultra, Prosep Ultraplus (which are manufactured by Merck millipore Corp.) or the like.

Examples of the gel filtration support may include a support composed of a polymer consisting of dextran, allyl dextran, N,N'-methylenebisacrylamide, cellulose, agarose, styrene, divinylbenzene, polyvinyl alcohol, silica, chitosan or the like, and specific examples thereof may include Sephacryl S series, Sepharose series, Sephadex series, Superdex series, Sephacryl series (which are manufactured by GE Healthcare Ltd., Inc.), TOYOPEARL HW series, TSKgel PW series (which are manufactured by TOSOH Corp.), Bio gel Agarose, Bio gel P Polyacrylamide (which are manufactured by Bio-Rad Inc.), Cellufine GH, Cellufine GCL (which are manufactured by JNC Corp.), Trisacryl GF05, Trisacryl GF2000, Ultrogel AcA (which are manufactured by Pall Corp.) or Fractogel BioSEC (manufactured by Merck millipore Corp.) or the like, but are not limited thereto.

The hydrophobic interaction support may be a support that is prepared by directly or indirectly immobilizing a hydrophobic molecule, for example, methyl group, ethyl group, propyl group, isopropyl group, butyl group, tert-butyl group, octyl group, ether group, phenyl group or the like onto the above base support, and specific examples thereof may include Phenyl Sepharose 6 Fast Flow (high-sub), Phenyl Sepharose 6 Fast Flow (low-sub), Octyl Sepharose 4 Fast Flow, Butyl Sepharose 4 Fast Flow (which are manufactured by GE Healthcare Ltd., Inc.), TOYOPEARL Hexyl-650, TOYOPEARL Butyl-650, TOYOPEARL Phenyl-650, TOYOPEARL Ether-650, TOYOPEARL PPG-600, TOYOPEARL Butyl-600, TOYOPEARL Super Butyl-550 (which are manufactured by TOSOH Corp.), Mactro-Prep t-Butyl, Macro-Prep Methyl (which are manufactured by Bio-Rad Inc.), QMA Spherosil, Methyl Ceramic HyperD (which are manufactured by Pall Corp.), Fractogel Phenyl(S), Fractogel Propyl(S) (which are manufactured by Merck millipore Corp.), phenyl-Cellufine (manufactured by JNC Corp.), DIAION HP, DIAION SP (which are manufactured by Mitsubishi Chemical Corp.), butylated Chitopearl, phenylated Chitopearl (which are manufactured by FUJIBO Holdings, Inc.) or the like.

The reverse phase support may be, for example, a support that is prepared by directly or indirectly immobilizing a hydrocarbon group onto a solid-phase matrix. Examples of the hydrocarbon group may include trimethyl group, butyl group, phenyl group, octyl group, octadecyl group, terminus-modified functional group thereof or the like. Specific examples thereof may include RESOURCE RPC series, SOURCE RPC series (which are manufactured by GE Healthcare Ltd., Inc.) or the like, but are not limited thereto.

Examples of the hydroxyapatite support may include CHT Ceramic Hydroxyapatite Type I, Type II (which are manufactured by Bio-Rad Inc.) or the like, but are not limited thereto. In addition, examples of the fluoroapatite support may include CFT Ceramic Fluoroapatite (manufactured by Bio-Rad Inc.) or the like, but are not limited thereto.

Examples of the cellulose sulfate support or the agarose sulfate support may include Cellufine sulfate, Cellufine sulfate m, Cellufine sulfate c, Cellulofine sulfate m, Cellulofine sulfate c, Cellufine sulfate m or Cellufine sulfate c (which are manufactured by JNC Corp.), Capto DeVirS (manufactured by GE Healthcare Ltd., Inc.) or the like, but are not limited thereto.

The multimodal support may be a support that is prepared by directly or indirectly immobilizing two or more types of functional groups having different selectivity, preferably, the above ion exchange group and the above hydrophobic interaction group, onto the above base support, and specific examples thereof may include Capto adhere, Capto MMC (which are manufactured by GE Healthcare Ltd., Inc.), HEA HyperCel, PPA HyperCel, MEP HyperCel (which are manufactured by Pall Corp.), TOYOPEARL MX-Trp-650M (manufactured by TOSOH Corp.) or the like, but are not limited thereto.

In the present invention, if the protein is an antibody, the protein-containing aqueous solution may be preferably a protein-containing aqueous solution that is obtained without using affinity chromatography, and more preferably, a protein-containing aqueous solution that is obtained without using protein A affinity chromatography.

Further, if insoluble materials such as particles or the like are present in the protein-containing aqueous solution, they are removed in advance, and the resulting insoluble-free solution may be provided in the purification method of the present invention. Examples of the method of removing insoluble materials such as particles may include centrifugation, cross-flow filtration (Tangential flow filtration), filtration using a depth filter, filtration using a membrane filter, dialysis, or combinations thereof. If necessary, the after-mentioned pH, conductivity, buffer, protein concentration of the protein-containing aqueous solution, or protein addition amount per unit volume of the activated carbon are adjusted, and then the resulting protein-containing aqueous solution may be provided in the purification method of the present invention.

Examples of the method of adjusting the pH, the conductivity, the buffer, the protein concentration, or the protein addition amount per unit volume of the activated carbon may include ultrafiltration using an ultrafiltration membrane or the like.

The ultrafiltration membrane includes a positively or negatively charged ultrafiltration membrane, in addition to the typical ultrafiltration membranes, and specific examples thereof may include Pellicon 3 Ultracel membrane, Pellicon 3 biomax membrane, Pellicon 2 Ultracel membrane, Pellicon 2 biomax membrane (which are manufactured by Merck millipore Corp.), omega membrane (manufactured by Pall Corp.), Kvick membrane (manufactured by GE Healthcare Ltd., Inc.) or the like, but are not limited thereto.

In the present invention, the impurities may include host cell proteins (HCP), protein-derived polymers, protein-derived degradation products, protein-derived modification products resulting from denaturation, removal of sugar chain components, oxidation, deamidation or the like, DNAs, medium-derived components, culture additives or enzymes secreted from host cells, and preferably host cell proteins, protein-derived polymers, protein-derived degradation products, or DNAs.

Examples of the enzymes secreted from host cells may include glycolytic enzymes, proteolytic enzymes, oxidation/reduction enzymes or the like.

Specific examples of the glycolytic enzymes may include neuraminidase (sialidase), galactosidase, glycanase or the like. Specific examples of the proteolytic enzymes may include serine protease, esterase, cysteine protease, trypsin-like protease, aminopeptidase, aspartic protease, cathepsin or the like. Specific examples of the oxidation/reduction enzymes may include thioredoxin-related enzymes such as thioredoxin reductase or the like. Specific examples of the amino acid isomerizing enzyme may include transglutaminase or the like.

The activated carbon used in the purification method of the present invention may be any one, as long as it is suitable for the drug preparation, and one type of activated carbon may be used alone, or two or more types of activated carbon may be used alone or in combination.

Examples of the activated carbon may include mineral-based activated carbon, plant-based activated carbon or the like. Specific examples of the mineral-based activated carbon may include coal-based activated carbon, petroleum-based activated carbon or the like, and specific examples of the plant-based activated carbon may include wood-based activated carbon, coconut-shell-based activated carbon or the like, and preferably wood-based activated carbon.

The raw material of the activated carbon may be any one, as long as it is carbonaceous, and examples thereof may include wood materials such as sawdust, charcoal, ash, peat moss, peat or wood chip, coconut-shell, coals such as lignite, brown coal or anthracite, coal pitch, petroleum pitch, oil carbon, rayon, acrylonitrile or phenol resin or the like.

The preparation method of the activated carbon is not particularly limited, but examples thereof may include a chemical liquid activation method of adding and penetrating a chemical such as zinc chloride or phosphoric acid at a high temperature and performing carbonization at a high temperature, or a gas activation method of reacting carbonized raw materials and gas such as water vapor, carbon dioxide, air or combustion gas at a high temperature.

The form of the activated carbon may be any one, as long as it is suitable for the drug preparation, and examples thereof may include a particle form of activated carbon, such as pulverized carbon, granular carbon, spherical carbon, pellet carbon or the like, a fibrous form of activated carbon such as fiber, cross fiber or the like, a specialized form of activated carbon such as a sheet form, a compact, a honeycomb shape or the like, powder activated carbon or the like.

The positively or negatively charged activated carbon or activated carbon modified with a surface modifier such as polyhydroxyethylmethacrylate (PHEMA), heparin, cellulose, polyurethane or the like may be also included in the activated carbon of the present invention.

An average micropore diameter of the activated carbon may be, but is not particularly limited to, typically 0.1 to 20 nm, preferably 0.5 to 5 nm, and more preferably 1 to 3 nm.

Specific examples thereof may include Carboraffin, strong SHIRASAGI, purified SHIRASAGI, specialized SHIRASAGI, SHIRASAGI A, SHIRASAGI C, SHIRASAGI C-1, SHIRASAGI DO-2, SHIRASAGI DO-5, SHIRASAGI DO-11, SHIRASAGI DC, SHIRASAGI DO, SHIRASAGI Gx, SHIRASAGI G, SHIRASAGI GH, SHIRASAGI FAC-10, SHIRASAGI M, SHIRASAGI P, SHIRASAGI PHC, SHIRASAGI Gc, SHIRASAGI GH, SHIRASAGI GM, SHIRASAGI GS, SHIRASAGI GT, SHIRASAGI GAA, SHIRASAGI GOC, SHIRASAGI GOX, SHIRASAGI APRC, SHIRASAGI TAC, SHIRASAGI MAC, SHIRASAGI XRC, SHIRASAGI NCC, SHIRASAGI SRCX, SHIRASAGI Wc, SHIRASAGI LGK, SHIRASAGI KL, SHIRASAGI WH, SHIRASAGI W, SHIRASAGI WHA, SHIRASAGI LH, SHIRASAGI KL, SHIRASAGI LGK, SHIRASAGI MAC-W, SHIRASAGI S, SHIRASAGI Sx, SHIRASAGI X2M, SHIRASAGI X7000, SHIRASAGI X7100, SHIRASAGI DX7-3, MOLSIEVON (which are manufactured by Japan EnviroChemicals, Ltd.), ACF, Taiko (which are manufactured by Fuji Chemical Corp.), GLC (manufactured by KURARAY CHEMICAL CO., Ltd.), Taiko S, Taiko K, Taiko Q (which are manufactured by FUTAMURA Chemical CO., Ltd.), GAC, CN, CG, CAP/CGP, SX, CA (which are manufactured by Norit Japan Co., Ltd.) or the like.

Examples of the means of the purification method of the present invention may include, but are not particularly limited to, a batch method, a membrane treatment method, column chromatography or the like. Depending on each means, a suitable form of the activated carbon is selected. If necessary, a particle form or the like prepared by encapsulating the activated carbon in a porous polymer or a gel, a membrane or cartridge form or the like prepared by adsorbing, fixing or molding the activated carbon using a support such as polypropylene or cellulose, or fiber or the like. Specific examples thereof may include a CUNO activated carbon filter cartridge, a Zeta plus activated carbon filter cartridge (manufactured by Sumitomo 3M Ltd.), a Millistak+ activated carbon filter (manufactured by Merck millipore Corp.), a SUPRA AKS filter (manufactured by Pall Corp.), Adol (manufactured by UNITIKA Ltd.), a K filter, an activated carbon sheet (which are manufactured by TOYOBO CO., Ltd), Hemax (manufactured by KURARAY Co., Ltd.), Hemosorba (manufactured by Asahi Kasei Medical Co., Ltd.), Hemocolumn (manufactured by TERUMO Corp.), Hecellose (manufactured by TEIJIN Ltd.) or the like.

Depending on the protein of interest and the means of the purification method, packing density, granularity, rigidity, drying loss, residue on ignition, specific surface area, pore volume, or pH, or the like of the used activated carbon may be properly selected.

The purification method of the present invention is preferably carried out in a non-adsorption mode. The non-adsorption mode means that the protein-containing aqueous solution is contacted with the activated carbon, and the protein of interest is not adsorbed onto the activated carbon to recover a non-adsorption fraction. In detail, the pH, the conductivity, the buffer, the protein concentration of the protein-containing aqueous solution, the protein addition amount per unit volume of the activated carbon, temperature, or contact time with the activated carbon are adjusted in advance, and then contacted with the activated carbon. Thus, the protein of interest is not adsorbed onto the activated carbon, but impurities are adsorbed onto the activated carbon, thereby recovering the non-adsorption fraction having the protein with a low content of impurities.

The pH of the protein-containing aqueous solution to be contacted with the activated carbon is preferably 2 to 9 and more preferably 3 to 8. In particular, if the protein is an antibody, the pH of the protein-containing aqueous solution to be contacted with the activated carbon is preferably 2 to 8, more preferably 3 to 7, much more preferably 4 to 6, and most preferably 4 to 5. In addition, examples of the salt constituting the protein-containing aqueous solution may include phosphate, citrate, acetate, succinate, maleate, borate, Tris(base), HEPES, MES, PIPES, MOPS, TES, Tricine or the like. The concentration thereof is preferably 0.01 mol/L to 0.5 mol/L. For example, these salts may be also used in combinations of 0.01 mol/L to 0.5 mol/L, preferably of 0.01 mol/L to 0.5 mol/L of other salts, such as sodium chloride, potassium chloride, calcium chloride, sodium citrate, sodium sulfate, ammonium sulfate or the like. The buffer components, for example, amino acids such as glycine, alanine, arginine, serine, threonine, glutamic acid, aspartic acid, histidine or the like, sugars such as glucose, sucrose, lactose, sialic acid or the like, or derivatives thereof may be used in combinations.

The temperature of the protein-containing aqueous solution to be contacted with the activated carbon is preferably from 4° C. to 60° C., more preferably from 10° C. to 50° C., and much more preferably from 20° C. to 40° C.

In the present invention, the non-adsorption fraction of the activated carbon is recovered, so as to obtain the protein with a low content of impurities in a high yield. In detail, with respect to the content of the impurities, the content of the host cell proteins is preferably 100000 ng or less per 1 mg of the protein, more preferably 10000 ng or less per 1 mg of the protein, and much more preferably 1000 ng or less per 1 mg of the protein, the content of the protein-derived polymers is preferably 5% or less, more preferably 4% or less, and much more preferably 3% or less, the content of the protein-derived degradation products is preferably 10% or less, more preferably 5% or less, much more preferably 4% or less, and most preferably 3% or less. The recovery rate is preferably 50% or higher, more preferably 60% or higher, and the reduction rate of the host cell proteins (HCP LRV)

is preferably 1 or higher, more preferably 1.5 or higher and much more preferably 2 or higher.

In the present invention, the recovery rate of the protein with a low content of impurities and the content of impurities may be determined by the analysis method typically used for protein purification. For example, the recovery rate may be determined by absorbance or affinity HPLC such as protein A, the content of the host cell proteins may be determined by ELISA (Enzyme-Linked Immunosorbent Assay), Western blotting, an electrochemiluminescence assay or the like, the content of the protein-derived polymers or the protein-derived degradation products may be determined by gel filtration HPLC, ion exchange HPLC, polyacrylamide gel electrophoresis, a light scattering method, an ultracentrifugal method or the like, DNAs were determined by Pico-green, Threshold, QPCR or the like.

Further, the present invention relates to a method for preparing a protein, comprising the step of separating the protein from impurities using the activated carbon to obtain the protein with a low content of impurities.

In the preparation method of the present invention, a purification method to be used in combination with the activated carbon may be any one as long as it is suitable for drug preparation, and examples thereof may include chromatography, alcohol fraction, removal of precipitates, salting out, buffer exchange, concentration, dilution, filtration, virus inactivation, virus removal or the like. These purification methods to be used in combination with the activated carbon may be used in combinations of a plurality of types and numbers thereof. The purification method to be used in combination with the activated carbon may be carried out either before or after the purification method using the activated carbon.

The support or membrane used in the chromatography to be used in combination with the activated carbon may include those similar to the above-mentioned affinity support, an ion exchange support, an ion exchange membrane, a gel filtration support, a hydrophobic interaction support, a reverse phase support, a hydroxyapatite support, a fluoroapatite support, a cellulose sulfate support, an agarose sulfate support, a multimodal support or the like.

In the present invention, if the protein is an antibody, the chromatography to be used in combination with the activated carbon may be preferably a preparation method comprising no affinity chromatography, and more preferably a preparation method comprising no protein A affinity chromatography. If the protein is an antibody, examples of the chromatography to be used in combination with the activated carbon may include ion exchange chromatography, multimodal chromatography or combinations thereof.

The chromatography to be used in combination with the activated carbon may be carried out in an adsorption mode or in a non-adsorption mode, depending on the purpose. Preferably, at least one of the chromatography to be used in combination with the activated carbon is carried out in the adsorption mode.

The adsorption mode in the chromatography means that an aqueous solution provided in the chromatography is contacted with the corresponding support or membrane, the protein of interest is adsorbed onto the corresponding support or membrane, if necessary, washing is performed, and then the protein of interest is eluted using a buffer of which pH, conductivity, buffer components, salt concentration or additive or the like is altered, thereby recovering the adsorption fraction. The non-adsorption mode in the chromatography means that an aqueous solution provided in the chromatography is contacted with the corresponding support or membrane, the protein of interest is not adsorbed onto the corresponding support or membrane, thereby recovering the non-adsorption fraction.

In the protein purification method of the present invention, all the chromatographies to be used in combination with the activated carbon may be, for example, a protein purification method that is carried out in the non-adsorption mode (All negative chromatography).

In the present invention, if the protein is an antibody, the purification method using the activated carbon is carried out, and subsequently, the non-adsorption mode-ion exchange chromatography is carried out, followed by the adsorption mode-cation exchange chromatography, or the purification method using the activated carbon is carried out, and subsequently, the adsorption mode-cation exchange chromatography is carried out, followed by non-adsorption mode-anion exchange chromatography.

The conditions of the aqueous solution provided in the chromatography to be used in combination with the activated carbon or the buffer used in washing are properly selected with respect to the pH, conductivity, buffer components, salt concentration, additives or the like.

In the selection of the chromatographic conditions, differences in the physicochemical characteristics between the protein of interest and the compounds desired to be separated, for example, differences in isoelectric point, charge, hydrophobicity, molecular size, or steric structure or the like may be utilized. The elution method of the adsorption mode may include a one step elution method of using a buffer having a specific salt concentration or pH to reduce affinity between the protein of interest and the support, a stepwise method of eluting the protein of interest by changing the salt concentration or pH in a stepwise manner, or a gradient method of eluting the protein of interest by continuously changing the salt concentration or pH.

Examples of the salt constituting the buffer may include phosphate, citrate, acetate, succinate, maleate, borate, Tris (base), HEPES, MES, PIPES, MOPS, TES, Tricine or the like. These salts may be used in combinations with other salts, for example, sodium chloride, potassium chloride, calcium chloride, sodium citrate, sodium sulfate or ammonium sulfate. The buffer components, for example, amino acids such as glycine, alanine, arginine, serine, threonine, glutamic acid, aspartic acid or histidine or the like, sugars such as glucose, sucrose, lactose, sialic acid or the like, or derivatives thereof or the like may be used in combinations.

In the preparation method of the present invention, the protein with a low content of impurities may be obtained in a high recovery rate. In detail, with respect to the content of the impurities, the content of the host cell proteins is preferably 100 ng or less per 1 mg of the protein, and more preferably 10 ng or less per 1 mg of the protein, the content of the protein-derived polymers is preferably 3.5% or less, and more preferably 1% or less, the content of the protein-derived degradation products is preferably 3.5% or less, and more preferably 1% or less. The recovery rate is preferably 30% or more, and more preferably 40% or more.

Hereinafter, the present invention will be described in more detail with reference to Examples. However, the present invention is not limited to these Examples.

EXAMPLES

Example 1: Mab A Purification 1 (Non-Adsorption Mode Purification Comprising Activated Carbon)

Approximately 600 mL of CHO cell culture supernatant containing monoclonal antibodies (Mab A) that were previously clarified by microfiltration was adjusted to pH 4.5 with acetic acid. The formed precipitates were removed by centrifugation and a filter. The resulting clarified solution was neutralized with a Tris solution, and concentrated to approximately 6-fold using a Pellicon 3 Ultracel membrane (manufactured by millipore Corp., 30 kD, 0.11 m$^2$). After concentration, the buffer was exchanged with 10 mmol/L Tris buffer (pH 8.0) to obtain a concentrated/buffer-exchanged solution.

Subsequently, Mab A purification comprising activated carbon was carried out in a non-adsorption mode by the following procedure. First, the resulting concentrated/buffer-exchanged solution was passed through an activated carbon filter (manufactured by CUNO Ltd., Zeta carbon filter, 25 cm$^2$), and pooled as an activated carbon eluate A.

The resulting activated carbon eluate A was applied to an anion exchange chromatography column (manufactured by GE Healthcare Ltd., Inc., Q Sepharose, 11 mm ID×20 cm) that was equilibrated with an equilibration buffer consisting of 10 mmol/L Tris buffer (pH 8.0). After completion of the application, 5 column volumes of the equilibration buffer were passed through the column. The column non-adsorbed fraction was pooled as a Q Sepharose eluate.

Approximately 10 mmol/L of sodium citrate was added to the resulting Q Sepharose eluate, and adjusted to pH 7.0 with hydrochloric acid, and then applied to a multimodal chromatography column (manufactured by GE Healthcare Ltd., Inc., Capto adhere, 10 mm ID×20 cm) that was equilibrated with an equilibration buffer prepared by adjusting 10 mmol/L Tris buffer (pH 8.0) to pH 7.0 with a citric acid solution. After completion of the application, the equilibration buffer was passed through the column. A part of the column non-adsorbed fraction was pooled as a Capto adhere eluate.

The resulting Capto adhere eluate was adjusted to pH 4.5 with acetic acid, and then passed through the activated carbon filter (manufactured by CUNO Ltd., Zeta carbon filter, 25 cm$^2$), and pooled as an activated carbon eluate B. The resulting activated carbon eluate B was used as a final Mab A purified product.

The contents of polymers and degradation products in the final Mab A purified product were analyzed by gel filtration HPLC, and the content of host cell proteins therein was analyzed by ELISA.

Figure 2:
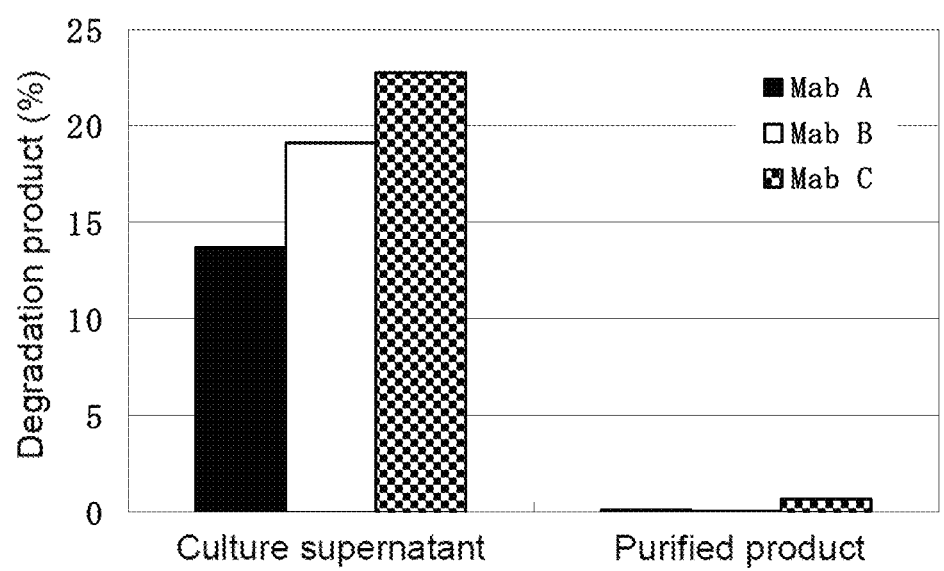
FIG. 2 shows the degradation product contents of the supernatant and the final purified product in non-adsorption mode comprising activated carbon purification of Mab A, Mab B and Mab C. The vertical axis represents the degradation product content (%), the black color represents Mab A, the white color represents Mab B, and the grey color represents Mab C. From left, the degradation product contents of the culture supernatant (Culture supernatant) and the final purified product (Purified product) are represented.
Figure 3:
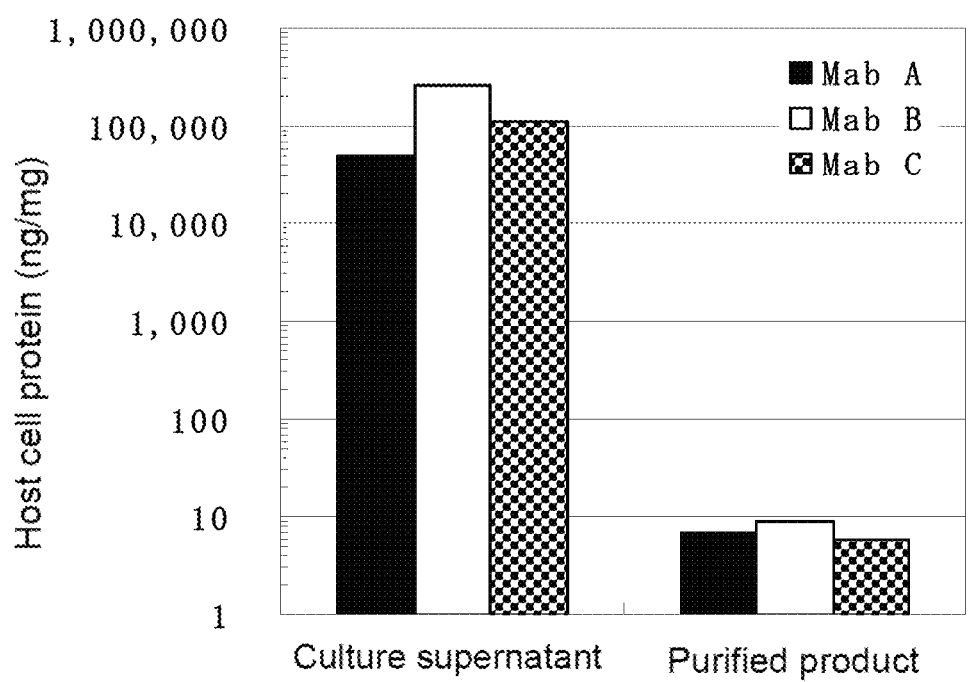
FIG. 3 shows the host cell protein contents of the supernatant and the final purified product in non-adsorption mode comprising activated carbon purification of Mab A, Mab B and Mab C. The vertical axis represents the host cell protein content per 1 mg of protein (ng/mg), the black color represents Mab A, the white color represents Mab B, and the grey color represents Mab C. From left, the host cell protein contents of the culture supernatant (Culture supernatant) and the final purified product (Purified product) are represented.

The analysis results of the final Mab A purified product are shown in FIGS. 1, 2, and 3. According to the present purification method, the Mab A purified product could be obtained, in which the contents of polymers and degradation products were less than 1%, respectively and the content of host cell proteins was less than 10 ng/mg.

Example 2: Mab B Purification 1 (Non-Adsorption Mode Purification Comprising Activated Carbon)

Approximately 600 mL of CHO cell culture supernatant containing monoclonal antibodies (Mab B) that were previously clarified by microfiltration was adjusted to pH 4.5 with acetic acid. The formed precipitates were removed by centrifugation and a filter. The resulting clarified solution was neutralized with a Tris solution, and concentrated to approximately 6-fold using the Pellicon 3 Ultracel membrane (manufactured by millipore Corp., 30 kD, 0.11 m$^2$). After concentration, the buffer was exchanged with 10 mmol/L Tris buffer (pH 8.0) to obtain a concentrated/buffer-exchanged solution.

Subsequently, Mab B purification comprising activated carbon was carried out in a non-adsorption mode by the following procedure. First, the resulting concentrated/buffer-exchanged solution was passed through the activated carbon filter (manufactured by CUNO Ltd., Zeta carbon filter, 25 cm$^2$), and pooled as an activated carbon eluate A.

The resulting activated carbon eluate A was applied to the anion exchange chromatography column (manufactured by GE Healthcare Ltd., Inc., Q Sepharose, 11 mm ID×20 cm) that was equilibrated with the equilibration buffer consisting of 10 mmol/L Tris buffer (pH 8.0). After completion of the application, 5 column volumes of the equilibration buffer were passed through the column. The column non-adsorbed fraction was pooled as a Q Sepharose eluate A.

Approximately 10 mmol/L of sodium citrate was added to the resulting Q Sepharose eluate A, and adjusted to pH 7.0 with hydrochloric acid, and then applied to the multimodal chromatography column (manufactured by GE Healthcare Ltd., Inc., Capto adhere, 10 mm ID×20 cm) that was equilibrated with the equilibration buffer prepared by adjusting 10 mmol/L Tris buffer (pH 8.0) to pH 7.0 with the citric acid solution. After completion of the application, the equilibration buffer was passed through the column. A part of the column non-adsorbed fraction was pooled as a Capto adhere eluate.

The resulting Capto adhere eluate was adjusted to pH 4.5 with acetic acid, and then passed through the activated carbon filter (manufactured by CUNO Ltd., Zeta carbon filter, 25 cm$^2$), and pooled as an activated carbon eluate B.

The resulting activated carbon eluate B was adjusted to pH 8.0 with the Tris solution, and then filtered using a filter to obtain a filtrate. The resulting filtrate was applied to the anion exchange chromatography column (manufactured by GE Healthcare Ltd., Inc., Q Sepharose, 11 mm ID×20 cm) that was equilibrated with the equilibration buffer consisting of 10 mmol/L Tris buffer (pH 8.0). After completion of the application, 5 column volumes of the equilibration buffer were passed through the column. The column non-adsorbed fraction was pooled as a Q Sepharose eluate B. The resulting Q Sepharose eluate B was used as a final Mab B purified product.

The contents of polymers, degradation products, and host cell proteins in the final Mab B purified product were analyzed in the same manner as in Example 1.

The analysis results of the final Mab B purified product are shown in FIGS. 1, 2, and 3. According to the present purification method, the Mab B purified product could be obtained, in which the contents of polymers and degradation products were less than 1%, respectively and the content of host cell proteins was less than 10 ng/mg.

Example 3: Mab C Purification 1 (Non-Adsorption Mode Purification Comprising Activated Carbon)

Approximately 600 mL of CHO cell culture supernatant containing monoclonal antibodies (Mab C) that were previously clarified by microfiltration was adjusted to pH 4.5 with acetic acid. The formed precipitates were removed by centrifugation and a filter. The resulting clarified solution was neutralized with a Tris solution, and concentrated to approximately 6-fold using the Pellicon 3 Ultracel membrane (manufactured by millipore Corp., 30 kD, 0.11 m$^2$). After concentration, the buffer was exchanged with 10 mmol/L Tris buffer (pH 7.1) to obtain a concentrated/buffer-exchanged solution.

Subsequently, Mab C purification comprising activated carbon was carried out in a non-adsorption mode by the following procedure. First, the resulting concentrated/buffer-exchanged solution was passed through the activated carbon filter (manufactured by CUNO Ltd., Zeta plus EXT charged depth filter, 25 cm$^2$), and pooled as an activated carbon eluate A.

The resulting activated carbon eluate A was applied to the anion exchange chromatography column (manufactured by GE Healthcare Ltd., Inc., Q Sepharose, 11 mm ID×20 cm) that was equilibrated with the equilibration buffer consisting of 10 mmol/L Tris buffer (pH 7.1). After completion of the application, 5 column volumes of the equilibration buffer were passed through the column. The column non-adsorbed fraction was pooled as a Q Sepharose eluate.

Approximately 10 mmol/L of citric acid/sodium citrate was added to the resulting Q Sepharose pooled solution, and adjusted to pH 6.0 with hydrochloric acid, and then applied to the multimodal chromatography column (manufactured by GE Healthcare Ltd., Inc., Capto adhere, 10 mm ID×20 cm) that was equilibrated with the equilibration buffer prepared by adjusting 10 mmol/L Tris buffer (pH 7.1) to pH 6.0 with the citric acid solution. After completion of the application, the equilibration buffer was passed through the column. A part of the column non-adsorbed fraction was pooled as a Capto adhere eluate.

The resulting Capto adhere eluate was adjusted to pH 4.5 with acetic acid, and then passed through the activated carbon filter (manufactured by CUNO Ltd., Zeta carbon filter, 25 cm$^2$), and pooled as an activated carbon eluate B. The resulting activated carbon eluate B was used as a final Mab C purified product.

The contents of polymers, degradation products, and host cell proteins in the final Mab C purified product were analyzed in the same manner as in Example 1.

The analysis results of the final Mab C purified product are shown in FIGS. 1, 2, and 3. According to the present purification method, the Mab C purified product could be obtained, in which the contents of polymers and degradation products were less than 1%, respectively and the content of host cell proteins was less than 10 ng/mg.

Example 4: Mab A Purification 2 (Non-Adsorption Mode Purification Comprising Activated Carbon)

Approximately 100 mL of CHO cell culture supernatant containing monoclonal antibodies (Mab A) that were previously clarified by microfiltration was adjusted to pH 4.5 with acetic acid. The formed precipitates were removed by centrifugation to obtain a clarified solution.

Subsequently, Mab A purification comprising activated carbon was carried out in a non-adsorption mode by the following procedure. First, the resulting clarified solution was passed through the activated carbon filter (manufactured by CUNO Ltd., Zeta carbon filter, 25 cm$^2$), and pooled as an activated carbon eluate A.

The resulting activated carbon eluate A was applied to the cation exchange chromatography column (manufactured by millipore Corp., ProRes S, 3 mm ID×20 cm) that was equilibrated with the equilibration buffer consisting of 10 mmol/L acetic acid buffer (pH 4.5). After completion of the application, 7 column volumes of the equilibration buffer were passed through the column. A part of the column non-adsorbed fraction was pooled as a ProRes S eluate.

The resulting ProRes S eluate was passed through the activated carbon filter (manufactured by CUNO Ltd., Zeta carbon filter, 25 cm$^2$), and pooled as an activated carbon eluate B.

The resulting activated carbon eluate B was diluted 4-fold using 5 mmol/L Tris buffer (pH 8.0) and then neutralized with the Tris solution, and filtered using a filter. Thereafter, the filtrate was applied to the anion exchange chromatography column (manufactured by GE Healthcare Ltd., Inc., Q Sepharose, 11 mm ID×20 cm) that was equilibrated with the equilibration buffer consisting of 10 mmol/L Tris buffer (pH 8.0). After completion of the application, 5 column volumes of the equilibration buffer were passed through the column. The column non-adsorbed fraction was pooled as a Q Sepharose eluate. The resulting Q Sepharose eluate was used as a final Mab A purified product.

The contents of polymers, degradation products, and host cell proteins in the final Mab A purified product were analyzed in the same manner as in Example 1.

Figure 4:
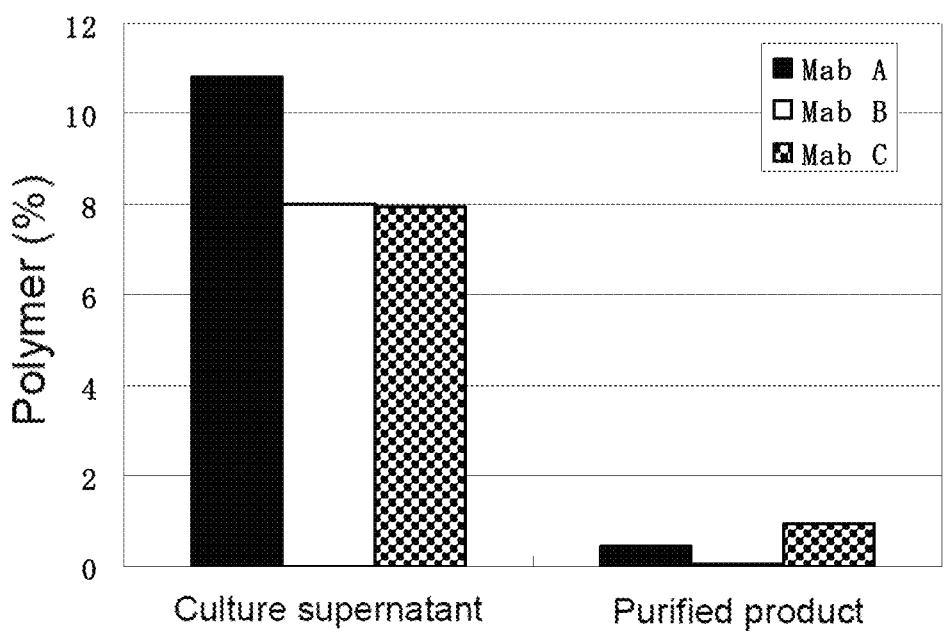
FIG. 4 shows the polymer contents of the supernatant and the final purified product in non-adsorption mode comprising activated carbon purification of Mab A, Mab B and Mab C. The vertical axis represents the polymer content (%), the black color represents Mab A, the white color represents Mab B, and the grey color represents Mab C. From left, the polymer contents of the culture supernatant (Culture supernatant) and the final purified product (Purified product) are represented.
Figure 5:
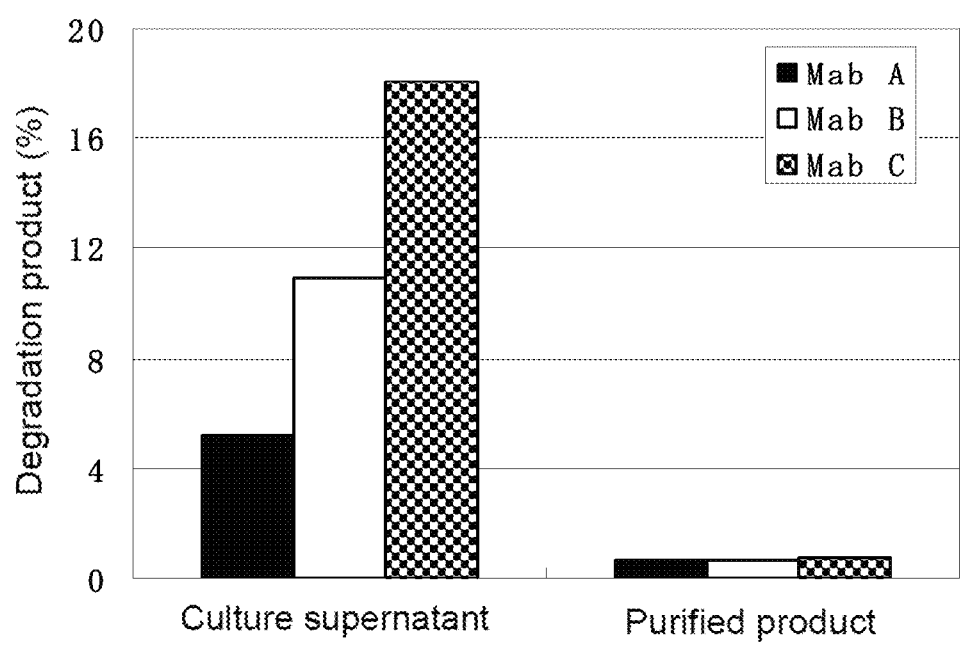
FIG. 5 shows the degradation product contents of the supernatant and the final purified product in non-adsorption mode comprising activated carbon purification of Mab A, Mab B and Mab C. The vertical axis represents the degradation product content (%), the black color represents Mab A, the white color represents Mab B, and the grey color represents Mab C. From left, the degradation product contents of the culture supernatant (Culture supernatant) and the final purified product (Purified product) are represented.
Figure 6:
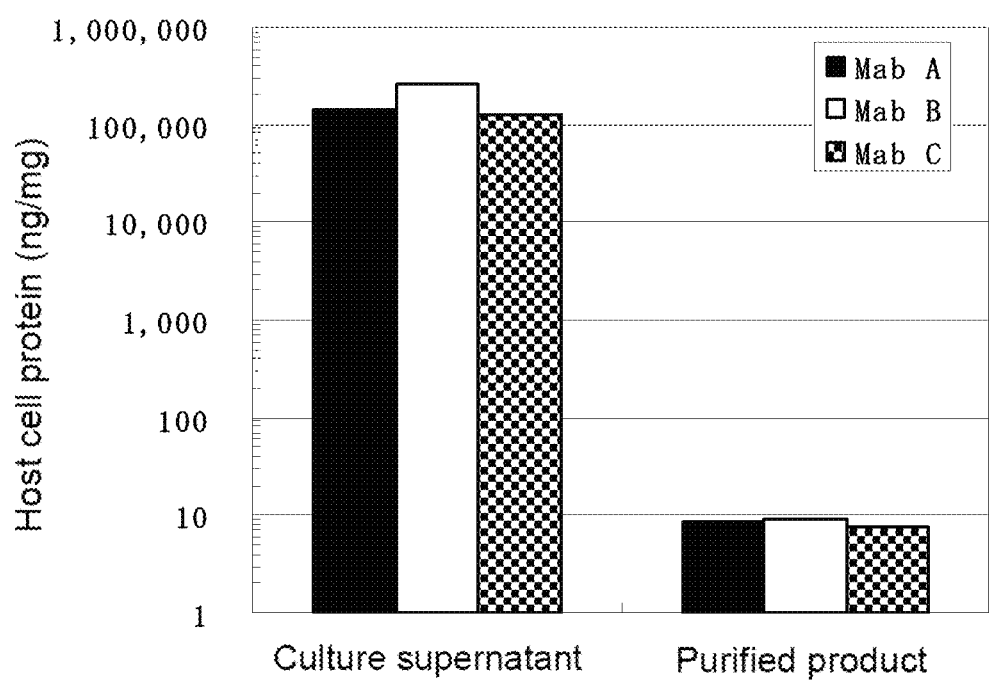
FIG. 6 shows the host cell protein contents of the supernatant and the final purified product in non-adsorption mode comprising activated carbon purification of Mab A, Mab B and Mab C. The vertical axis represents the host cell protein content per 1 mg of protein (ng/mg), the black color represents Mab A, the white color represents Mab B, and the grey color represents Mab C. From left, the host cell protein contents of the culture supernatant (Culture supernatant) and the final purified product (Purified product) are represented.

The analysis results of the final Mab A purified product are shown in FIGS. 4, 5, and 6. According to the present purification method, the Mab A purified product could be obtained, in which the contents of polymers and degradation products were less than 1%, respectively and the content of host cell proteins was less than 10 ng/mg.

Example 5: Mab B Purification 2 (Non-Adsorption Mode Purification Comprising Activated Carbon)

Approximately 100 mL of CHO cell culture supernatant containing monoclonal antibodies (Mab B) that were previously clarified by microfiltration was adjusted to pH 4.5 with acetic acid. The formed precipitates were removed by centrifugation to obtain a clarified solution.

Subsequently, Mab B purification comprising activated carbon was carried out in a non-adsorption mode by the following procedure. First, the resulting clarified solution was passed through the activated carbon filter (manufactured by CUNO Ltd., Zeta carbon filter, 25 cm$^2$), and pooled as an activated carbon eluate A.

The resulting activated carbon eluate A was applied to the cation exchange chromatography column (manufactured by millipore Corp., ProRes S, 3 mm ID×20 cm) that was equilibrated with the equilibration buffer consisting of 10 mmol/L acetic acid buffer (pH 4.5). After completion of the application, 7 column volumes of the equilibration buffer were passed through the column. A part of the column non-adsorbed fraction was pooled as a ProRes S eluate.

The resulting ProRes S eluate was passed through the activated carbon filter (manufactured by CUNO Ltd., Zeta carbon filter, 25 cm$^2$), and pooled as an activated carbon eluate B.

The resulting activated carbon eluate B was diluted 4-fold using 5 mmol/L Tris buffer (pH 8.0) and then neutralized with the Tris solution, and filtered using a filter. Thereafter, the filtrate was applied to the anion exchange chromatography column (manufactured by GE Healthcare Ltd., Inc., Q Sepharose, 11 mm ID×20 cm) that was equilibrated with the equilibration buffer consisting of 10 mmol/L Tris buffer (pH 8.0). After completion of the application, 5 column volumes of the equilibration buffer were passed through the column. The column non-adsorbed fraction was pooled as a Q Sepharose eluate. The resulting Q Sepharose eluate was used as a final Mab B purified product.

The contents of polymers, degradation products, and host cell proteins in the final Mab B purified product were analyzed in the same manner as in Example 1.

The analysis results of the final Mab B purified product are shown in FIGS. 4, 5, and 6. According to the present purification method, the Mab B purified product could be obtained, in which the contents of polymers and degradation products were less than 1%, respectively and the content of host cell proteins was less than 10 ng/mg.

Example 6: Mab C Purification 2 (Non-Adsorption Mode Purification Comprising Activated Carbon)

Approximately 100 mL of CHO cell culture supernatant containing monoclonal antibodies (Mab C) that were previously clarified by microfiltration was adjusted to pH 4.5 with acetic acid. The formed precipitates were removed by centrifugation to obtain a clarified solution.

Subsequently, Mab C purification comprising activated carbon was carried out in a non-adsorption mode by the following procedure. First, the resulting clarified solution was passed through the activated carbon filter (manufactured by CUNO Ltd., Zeta carbon filter, 25 cm$^2$), and pooled as an activated carbon eluate A.

The resulting activated carbon eluate A was applied to the cation exchange chromatography column (manufactured by millipore Corp., ProRes S, 3 mm ID×20 cm) that was equilibrated with the equilibration buffer consisting of 10 mmol/L acetic acid buffer (pH 4.5). After completion of the application, 5 column volumes of the equilibration buffer were passed through the column. A part of the column non-adsorbed fraction was pooled as a ProRes S eluate.

The resulting ProRes S eluate was passed through the activated carbon filter (manufactured by CUNO Ltd., Zeta carbon filter, 25 cm$^2$), and pooled as an activated carbon eluate B.

The resulting activated carbon eluate B was diluted 4-fold using 5 mmol/L Tris buffer (pH 7.0) and then neutralized with the Tris solution, and filtered using a filter. Thereafter, the filtrate was applied to the anion exchange chromatography column (manufactured by GE Healthcare Ltd., Inc., Q Sepharose, 11 mm ID×20 cm) that was equilibrated with the equilibration buffer consisting of 10 mmol/L Tris buffer (pH 7.0). After completion of the application, 5 column volumes of the equilibration buffer were passed through the column. The column non-adsorbed fraction was pooled as a Q Sepharose eluate. The resulting Q Sepharose eluate was used as a final Mab C purified product.

The contents of polymers, degradation products, and host cell proteins in the final Mab C purified product were analyzed in the same manner as in Example 1.

The analysis results of the final Mab C purified product are shown in FIGS. 4, 5, and 6. According to the present purification method, the Mab C purified product could be obtained, in which the contents of polymers and degradation products were less than 1%, respectively and the content of host cell proteins was less than 10 ng/mg.

Example 7: Mab A Purification 3 (Purification Comprising Activated Carbon)

Approximately 200 mL of CHO cell culture supernatant containing monoclonal antibodies (Mab A) that were clarified by microfiltration was adjusted to pH 4.5 with acetic acid. The formed precipitates were removed by centrifugation to obtain a clarified solution A.

Subsequently, activated carbon (manufactured by Japan EnviroChemicals, Ltd, SHIRASAGI P) was added to approximately 60 mL of the resulting clarified solution A, and mixed. Thereafter, the mixture was subjected to centrifugation and filtration using a filter to obtain an activated carbon eluate.

The resulting activated carbon eluate was diluted 4-fold using 5 mmol/L Tris buffer, and then adjusted to pH 8.0 with the Tris solution. Thereafter, the resultant was applied to the anion exchange chromatography column (manufactured by GE Healthcare Ltd., Inc., Q Sepharose, 5 mm ID×20 cm) that was equilibrated with the equilibration buffer consisting of 10 mmol/L Tris buffer (pH 8.0). After completion of the application, 5 column volumes of the equilibration buffer were passed through the column. The column non-adsorbed fraction was pooled as a Q Sepharose eluate.

The resulting Q Sepharose eluate was adjusted to pH 5.0 with the acetic acid solution. Thereafter, the resultant was applied to the cation exchange chromatography column (manufactured by Applied Biosystems, POROS XS, 5 mm ID×20 cm) that was equilibrated with the equilibration buffer consisting of 10 mmol/L acetic acid buffer (pH 5.0). After completion of the application, 5 column volumes of the equilibration buffer were passed through the column. Next, elution was carried out with a salt concentration gradient (10-column volumes) of gradually increasing the salt concentration in a 10 mmol/L acetic acid buffer (pH 5.0) containing 0.3 mol/L sodium chloride. A part of the column-eluted fraction was pooled as a POROS XS eluate. The POROS XS eluate was used as a final Mab A purified product.

Example 8: Mab B Purification 3 (Purification Comprising Activated Carbon)

Approximately 225 mL of CHO cell culture supernatant containing monoclonal antibodies (Mab B) that were clarified by microfiltration was adjusted to pH 4.5 with acetic acid. The formed precipitates were removed by centrifugation to obtain a clarified solution B.

Subsequently, activated carbon (manufactured by Japan EnviroChemicals, Ltd, SHIRASAGI P) was added to approximately 60 mL of the resulting clarified solution B, and mixed. Thereafter, the mixture was subjected to centrifugation and filtration using a filter to obtain an activated carbon eluate.

The resulting activated carbon eluate was diluted 4-fold using 5 mmol/L Tris buffer, and then adjusted to pH 8.0 with the Tris solution. Thereafter, the resultant was applied to the anion exchange chromatography column (manufactured by GE Healthcare Ltd., Inc., Q Sepharose, 5 mm ID×20 cm) that was equilibrated with the equilibration buffer consisting of 10 mmol/L Tris buffer (pH 8.0). After completion of the application, 5 column volumes of the equilibration buffer were passed through the column. The column non-adsorbed fraction was pooled as a Q Sepharose eluate.

The resulting Q Sepharose eluate was adjusted to pH 5.1 with the acetic acid solution. Thereafter, the resultant was applied to the cation exchange chromatography column (manufactured by Applied Biosystems, POROS XS, 5 mm ID×20 cm) that was equilibrated with the equilibration buffer consisting of 10 mmol/L acetic acid buffer (pH 5.0). After completion of the application, 5 column volumes of the equilibration buffer were passed through the column. Next, elution was carried out with a salt concentration gradient (10-column volumes) of gradually increasing the salt concentration from 10 mmol/L acetic acid buffer (pH 5.0) containing 0.3 mol/L sodium chloride. A part of the column-eluted fraction was pooled as a POROS XS eluate. The POROS XS eluate was used as a final Mab B purified product.

Example 9: Analysis of Mab A Purified Product and Mab B Purified Product

The Mab A purification intermediate and the final purified product obtained in Example 7 and Comparative Example 1, and the Mab B purification intermediate and the final purified product obtained in Example 8 and Comparative Example 2 was analyzed out as follows.

The recovery rate of each purification process and the total recovery rate of the entire purification process were analyzed by protein A affinity HPLC.

Figure 7:
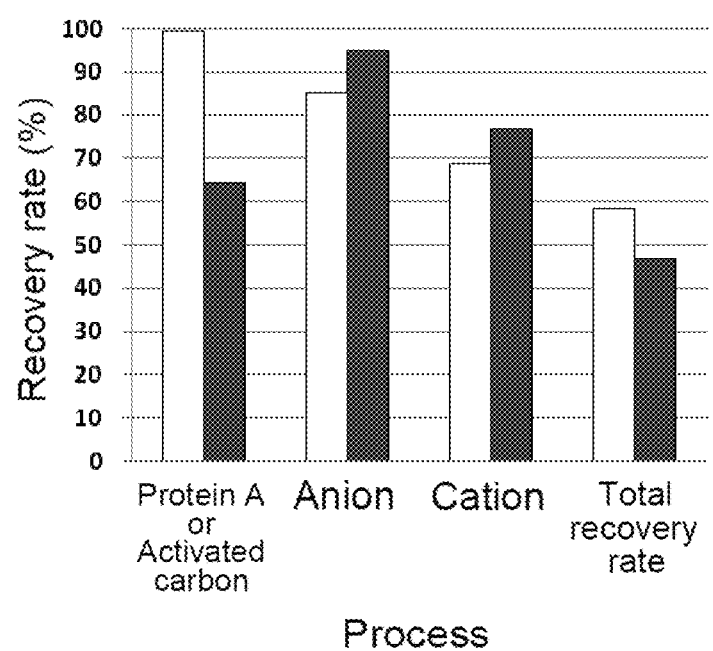
FIG. 7 shows the recovery rate of each process and the total recovery rate in the Mab A purification. The vertical axis represents the recovery rate of each process (%) or the total recovery rate (%), the white color represents purification comprising protein A affinity chromatography, the black color represents purification comprising activated carbon treatment. From left, the recovery rate of MabS elect SuRe treatment or activated carbon treatment (Protein A or Activated carbon), the recovery rate of Q Sepharose treatment (Anion), the recovery rate of POROS XS treatment (Cation), and the total recovery rate (Total recovery rate) are represented.
Figure 8:
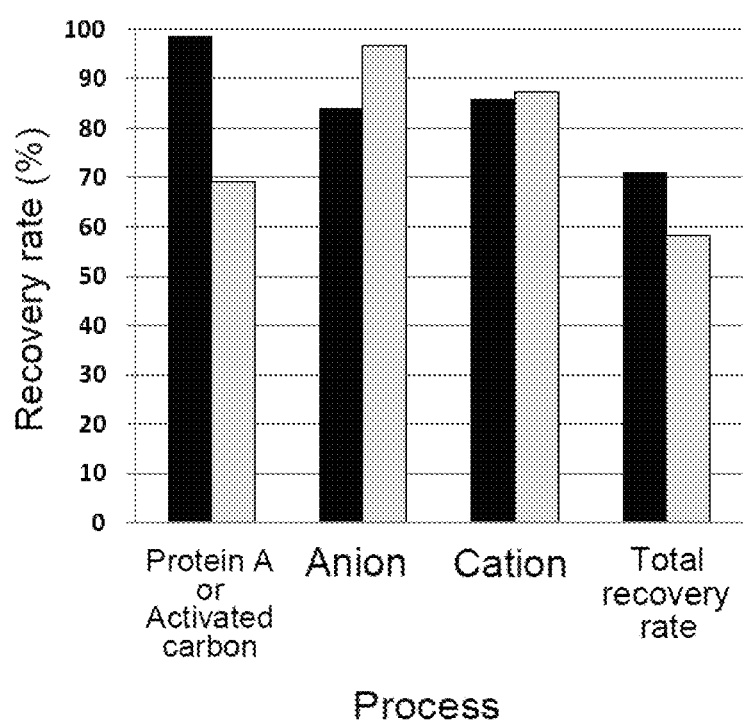
FIG. 8 shows the recovery rate of each process and the total recovery rate in the Mab B purification. The vertical axis represents the recovery rate of each process (%) or the total recovery rate (%), the black color represents purification comprising protein A affinity chromatography, and the grey color represents purification comprising activated carbon treatment. From left, the recovery rate of MabSelect SuRe treatment or activated carbon treatment (Protein A or Activated carbon), the recovery rate of Q Sepharose treatment (Anion), the recovery rate of POROS XS treatment (Cation), and the total recovery rate (Total recovery rate) are represented.

The results of recovery rate of each process and total recovery rate in the Protein A purification and the activated carbon purification of Mab A and Mab B are shown in FIGS. 7 and 8.

The total recovery rate of the activated carbon purification was almost equal to that of the protein A purification, and the recovery rate was as high as 40% or more.

The contents of the polymers and the degradation products in the purification intermediate and the final purified product were analyzed by gel filtration HPLC.

Figure 9:
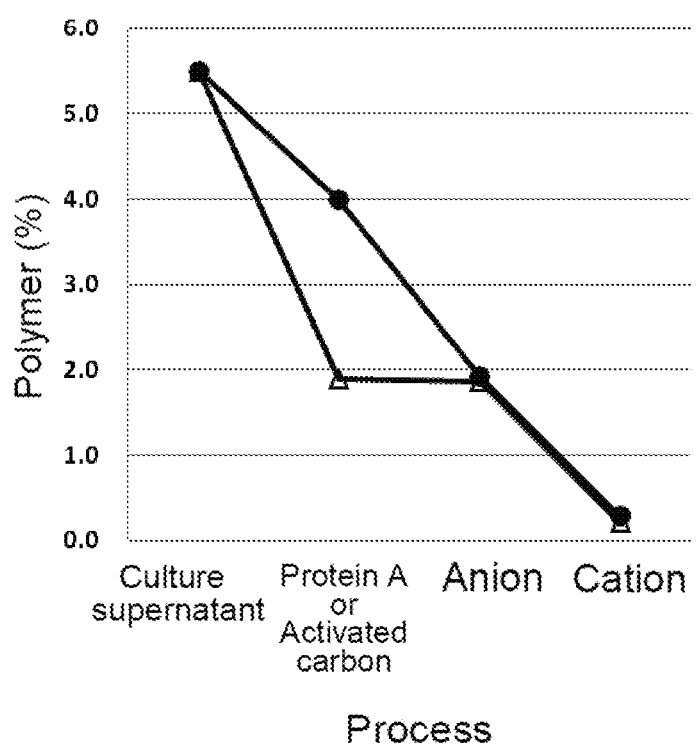
FIG. 9 shows the polymer contents of the purification intermediate and the final purified product in the Mab A purification. The vertical axis represents the polymer content (%). The black circle represents purification comprising protein A affinity chromatography, and the white triangle represents purification comprising activated carbon treatment. From left, the polymer contents of the clarified solution A (Supernatant), the MabSelect SuRe eluate or the activated carbon eluate (Protein A or Activated carbon), the Q Sepharose eluate (Anion), and the final Mab A purified product (Cation) are represented.
Figure 10:
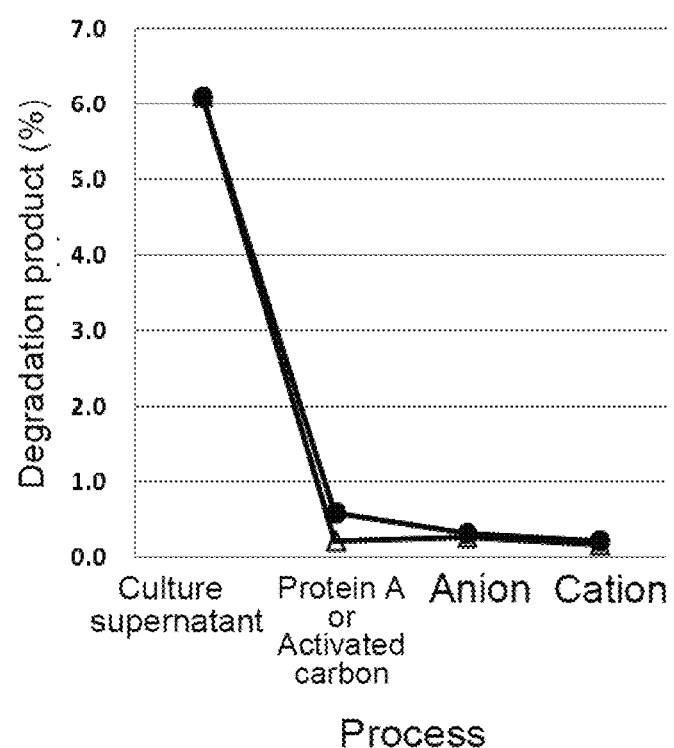
FIG. 10 shows the degradation product contents of the purification intermediate and the final purified product in the Mab A purification. The vertical axis represents the degradation product content (%). The black circle represents purification comprising protein A affinity chromatography, and the white triangle represents purification comprising activated carbon treatment. From left, the degradation product contents of the clarified solution A (Supernatant), the MabSelect SuRe eluate or the activated carbon eluate (Protein A or Activated carbon), the Q Sepharose eluate (Anion), and the final Mab A purified product (Cation) are represented.
Figure 11:
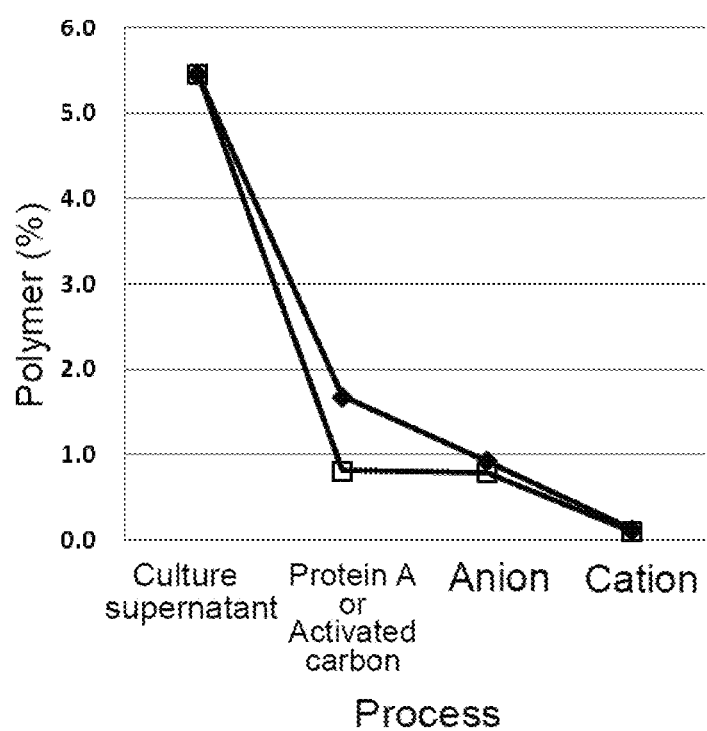
FIG. 11 shows the polymer contents of the purification intermediate and the final purified product in the Mab B purification. The vertical axis represents the polymer content (%). The black diamond represents purification comprising protein A affinity chromatography, and the white square represents purification comprising activated carbon treatment. From left, the polymer contents of the clarified solution B (Supernatant), the MabSelect SuRe eluate or the activated carbon eluate (Protein A or Activated carbon), the Q Sepharose eluate (Anion), and the final Mab B purified product (Cation) are represented.
Figure 12:
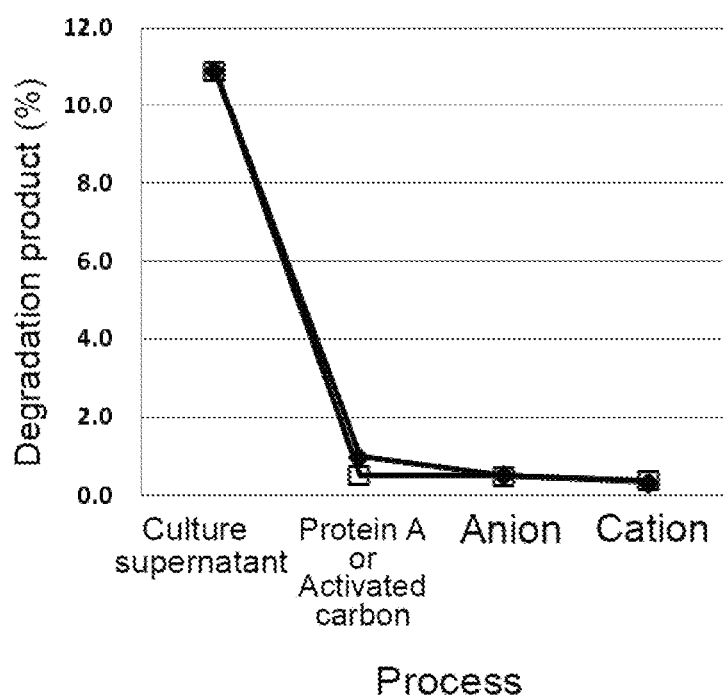
FIG. 12 shows the degradation product contents of the purification intermediate and the final purified product in the Mab B purification. The vertical axis represents the degradation product content (%). The black diamond represents purification comprising protein A affinity chromatography, and the white square represents purification comprising activated carbon treatment. From left, the degradation product contents of the clarified solution B (Supernatant), the MabSelect SuRe eluate or the activated carbon eluate (Protein A or Activated carbon), the Q Sepharose eluate (Anion), and the final Mab B purified product (Cation) are represented.

With respect to the purification intermediate and the final purified product in the protein A purification and the activated carbon purification of Mab A and Mab B, the contents of the polymers are shown in FIGS. 9 and 11, and the contents of the degradation products are shown in FIGS. 10 and 12, respectively.

Irrespective of the type of monoclonal antibodies, both of the purification methods showed that contents of the polymers and the degradation products in the final purified product (cation) were equivalent. Meanwhile, when the contents of the polymers and the degradation products were compared between the protein A purification process and the activated carbon purification process, the activated carbon purification process showed lower contents of the polymers and the degradation products than the protein A purification process, in which the contents were less than 2%.

The contents of the host cell proteins per 1 mg of protein in the purification intermediate and the final purified product were analyzed by ELISA.

Figure 13:
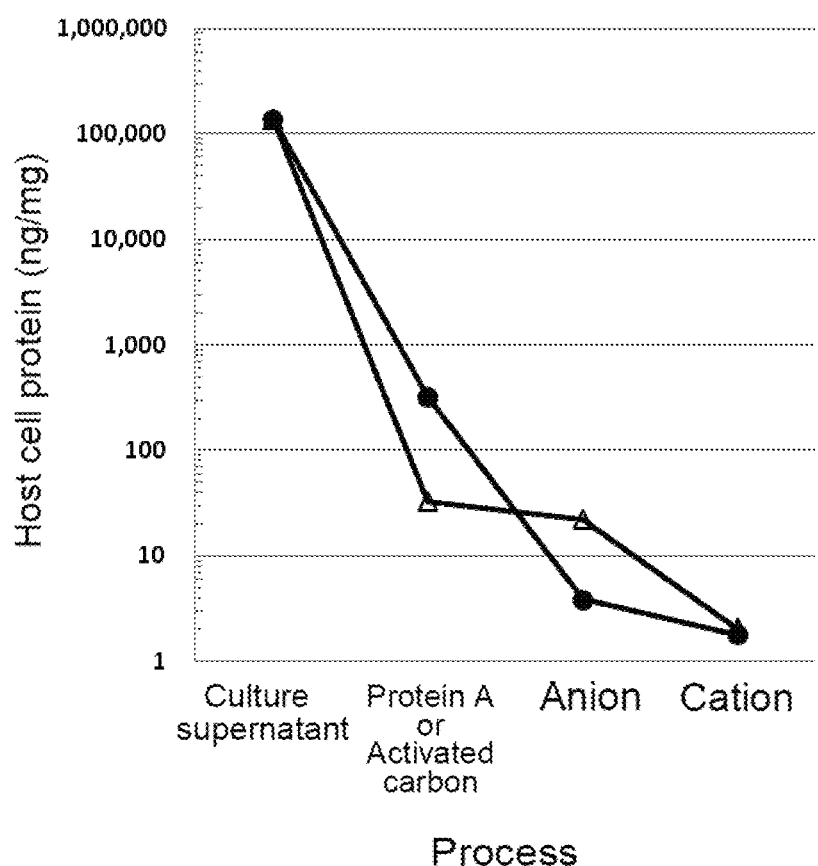
FIG. 13 shows the host cell protein contents of the purification intermediate and the final purified product in the Mab A purification. The vertical axis represents the content of the host cell protein per 1 mg of protein (ng/mg). The black circle represents purification comprising protein A affinity chromatography, and the white triangle represents purification comprising activated carbon treatment. From left, the host cell protein contents of the clarified solution A (Supernatant), the MabSelect SuRe eluate or the activated carbon eluate (Protein A or Activated carbon), the Q Sepharose eluate (Anion), and the final Mab A purified product (Cation) are represented.
Figure 14:
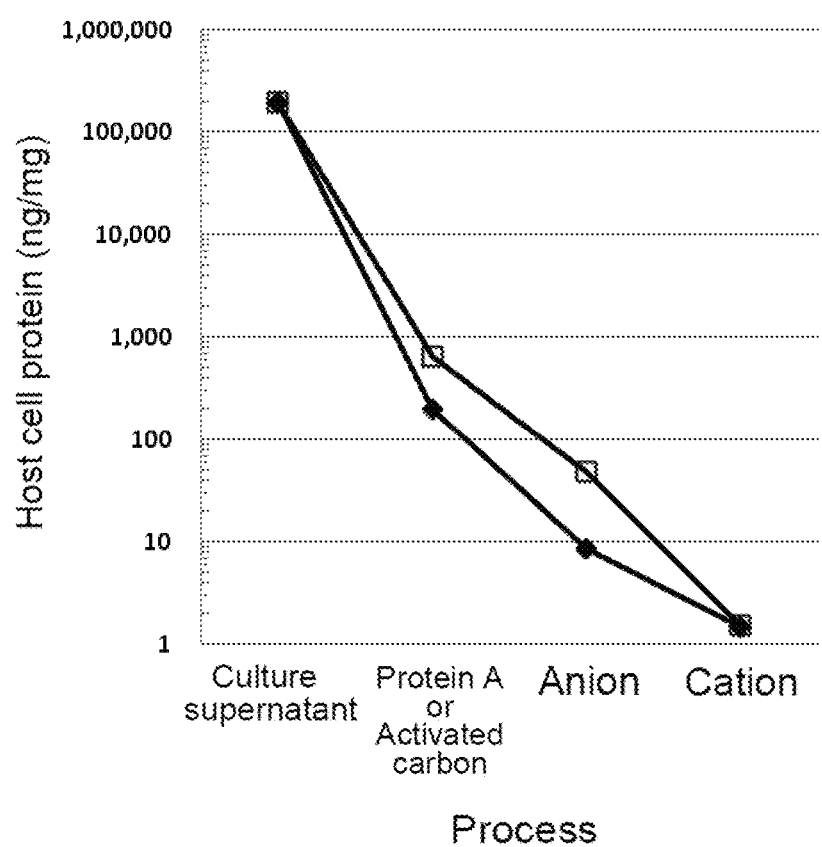
FIG. 14 shows the host cell protein contents of the purification intermediate and the final purified product in the Mab B purification. The vertical axis represents the content of the host cell protein per 1 mg of protein (ng/mg). The black diamond represents purification comprising protein A affinity chromatography, and the white square represents purification comprising activated carbon treatment. From left, the host cell protein contents of the clarified solution A (Supernatant), the MabSelect SuRe eluate or the activated carbon eluate (Protein A or Activated carbon), the Q Sepharose eluate (Anion), and the final Mab B purified product (Cation) are represented.

With respect to the protein A purification and the activated carbon purification of Mab A and Mab B, the contents of the host cell proteins per 1 mg of protein in the purification intermediate and the final purified product are shown in FIGS. 13 and 14.

Irrespective of the type of monoclonal antibodies, the protein A purification and the activated carbon purification showed that contents of the host cell proteins were equivalent. The contents of the host cell proteins in the final purified products were also equivalent, in which the contents were less than 10 ng/mg of protein.

These results showed that the contents of the host cell proteins in the purification intermediates were equivalent between the protein A purification and the activated carbon purification, whereas the activated carbon purification showed lower contents of the polymers and the degradation products, indicating that the proteins with much lower content of impurities can be obtained by the activated carbon purification.

Example 10: Inhibition of Antibody Degradation by Activated Carbon

The cell culture supernatant containing monoclonal antibodies (Mab B) was adjusted to pH 4.5 with acetic acid. The formed precipitates were removed using a filter to obtain a clarified solution.

Subsequently, the activated carbon (manufactured by Japan EnviroChemicals, Ltd, SHIRASAGI P) was added to the resulting clarified solution, and mixed. After retaining for 24 hours, the supernatant from which the activated carbon was removed was provided for SDS-PAGE analysis.

As a control, the solution without addition of the activated carbon was manipulated in the same manner as above, and provided for SDS-PAGE analysis under non-reduction conditions.

Figure 15:
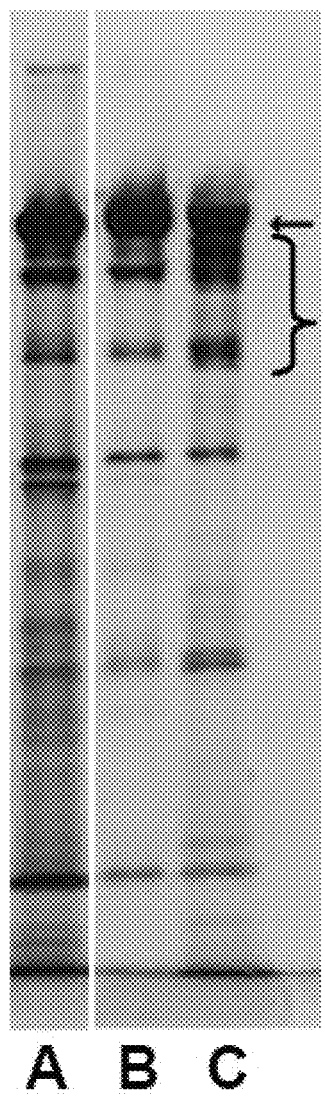
FIG. 15 shows SDS-PAGE of the Mab B culture supernatant. From left, (A) the clarified solution, (B) the supernatant that was maintained under addition of activated carbon for 24 hours and then the activated carbon was removed therefrom, and (C) the supernatant that was maintained for 24 hours without addition of activated carbon are represented.

The results of SDS-PAGE analysis are shown in FIG. 15. The control (C) showed stronger bands of the degradation products than the clarified solution (A), and the addition of the activated carbon (B) caused no strong band of the degradation products.

These results indicate that formation of degradation products was inhibited by addition of activated carbon.

Example 11: Inhibition of Antibody Reduction by Activated Carbon

The activated carbon (manufactured by Japan EnviroChemicals, Ltd, SHIRASAGI P) was added to the cell culture supernatant containing monoclonal antibodies (Mab D), and mixed. After removing the activated carbon, the supernatant was maintained under anaerobic conditions for 24 hours. After retaining 24 hours, the supernatant was provided for SDS-PAGE analysis under non-reduction conditions. As a control, the solution without addition of the activated carbon was manipulated in the same manner as above, and provided for SDS-PAGE analysis.

Figure 16:
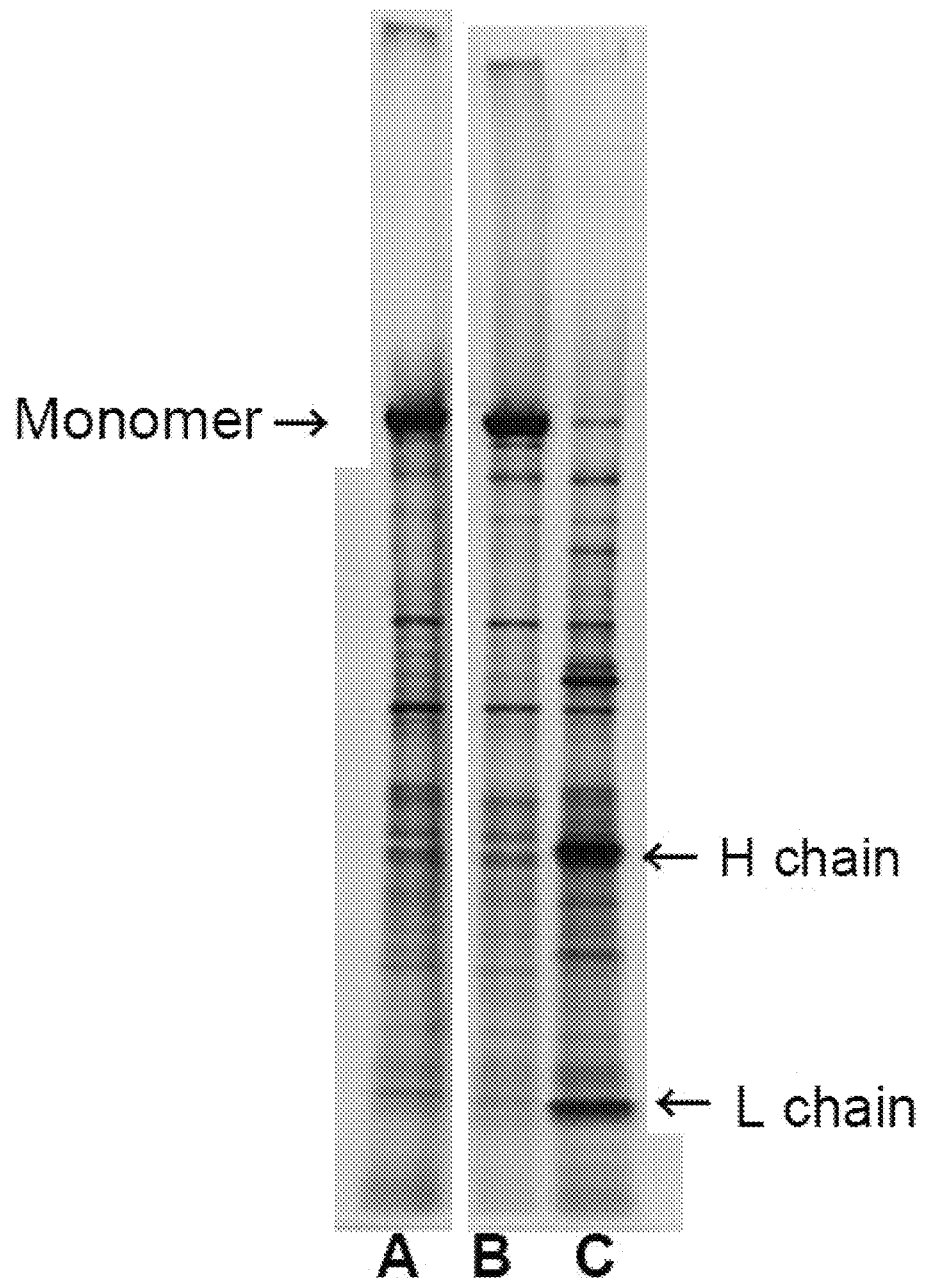
FIG. 16 shows SDS-PAGE of the Mab D culture supernatant. From left, (A) the supernatant, (B) the supernatant that was treated with addition/removal of activated carbon and maintained for 24 hours, and (C) the supernatant that was only treated with removal and maintained for 24 hours are represented.

The results of SDS-PAGE analysis are shown in FIG. 16. The bands (H chain, L chain) corresponding to antibody reduction were observed in the control (C), compared to the culture supernatant (A), but no bands (H chain, L chain) corresponding to antibody reduction were observed in the activated carbon treatment (B).

These results indicate that formation of reduced products was inhibited by addition of activated carbon.

Example 12: DNA Analysis of Mab A Purified Product and Mab B Purified Product DNA analysis of the final Mab A purified product obtained in Example 7, the Mab A purified product obtained in Comparative Example 1, the final Mab B purified product obtained in Example 8, and the Mab B purified product obtained in Comparative Example 2 was carried out by Threshold method.

Figure 17:
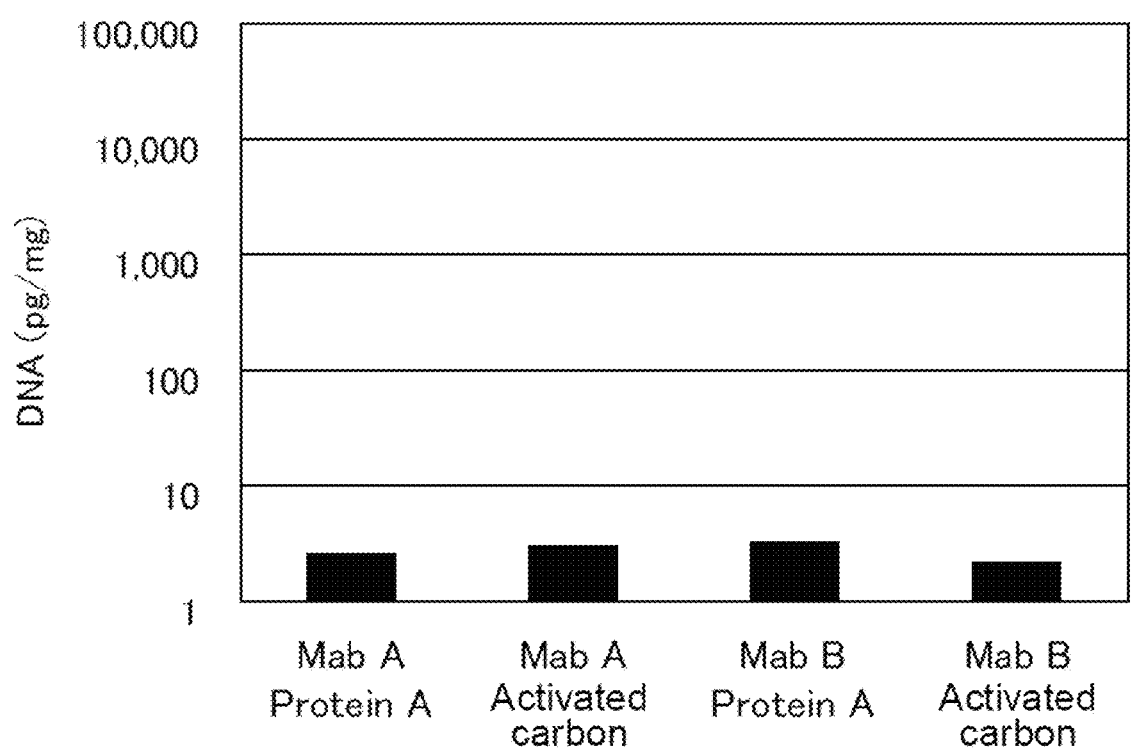
FIG. 17 shows DNA contents per 1 mg protein in the final purified product of activated carbon purification and the purified product of Protein A purification, with respect to Mab A and Mab B. The vertical axis represents the content of DNA per 1 mg of protein (pg/mg). From left, the DNA contents per 1 mg protein in the Mab A purified product of Protein A purification that was obtained by Comparative Example 1 (Mab A Protein A), the final Mab A purified product of activated carbon purification that was obtained by Example 7 (Mab A activated carbon), the Mab B purified product of Protein A purification that was obtained by Comparative Example 2 (Mab B Protein A), and the final Mab B purified product of activated carbon purification that was obtained by Example 8 (Mab B activated carbon) are represented.

DNA contents per 1 mg of the proteins in the final purified product of the activated carbon purification and in the purified product of the Protein A purification with respect to Mab A and Mab B are shown in FIG. 17.

The DNA contents of the final purified product and the purified product are equivalent between both purifications, in which the contents were 10 pg/mg or less.

Example 13: pH Effect in Activated Carbon Purification

The CHO cell culture supernatants containing monoclonal antibodies (Mab B) clarified by microfiltration were adjusted to pH 4, pH 5, pH 6, pH 7, pH 8 with an acid or an alkali, respectively. The formed precipitates were removed by a filter to obtain pH-adjusted clarified solutions.

Subsequently, the activated carbon (manufactured by Japan EnviroChemicals, Ltd, SHIRASAGI P) was added to approximately 10 mL of each of the pH-adjusted clarified solutions, and mixed. Then, each mixture was centrifuged to obtain each activated carbon eluate. Each of the pH-adjusted clarified solutions without addition of the activated carbon was used as each of pH control.

With respect to each of the pH-adjusted activated carbon eluates and each of the pH controls, the contents of the host cell proteins per 1 mg of protein were analyzed by ELISA.

The reduction rates of host cell proteins (HCP LRV) were calculated using the contents of the host cell proteins per 1 mg of protein by the following Equation.

reduction rate of host cell protein (HCP LRV)=−Log$_{10}$(content of host cell protein per 1 mg of protein of activated carbon eluate/content of host cell protein per 1 mg of protein of control)   (Equation)

Figure 18:
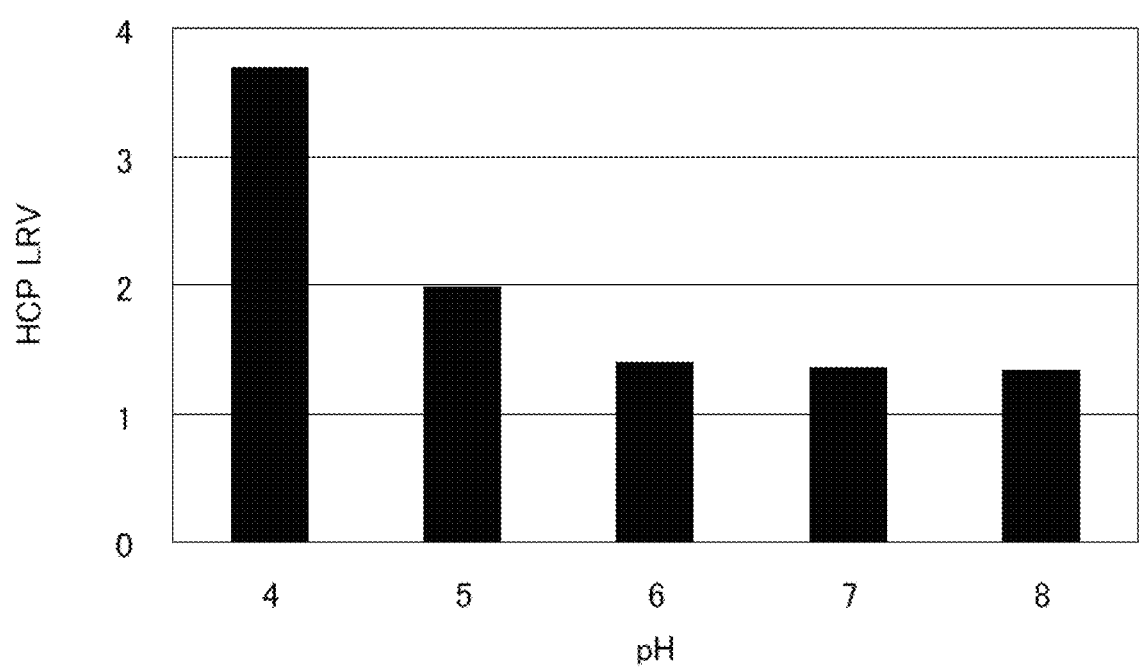
FIG. 18 shows the reduction rate of host cell proteins of activated carbon eluate at each pH by treatment of Mab B with activated carbon. The vertical axis represents the reduction rate of host cell protein of activated carbon eluate (HCP LRV). From left, the reduction rates of host cell protein of activated carbon eluate at pH 4, pH 5, pH 6, pH 7, and pH 8 are represented.

The reduction rates of host cell proteins (HCP LRV) at each pH by the activated carbon treatment are shown in FIG. 18. HCP LRV was 2 or higher at pH 4 and 5. HCP LRV was in the range of 1~2 at pH 6, pH 7 and pH 8. Therefore, it was found that the effect of activated carbon treatment on host cell protein reduction was higher at pH 4 and 5 than at pH 6, pH 7 and pH 8.

The antibody concentration of each pH activated carbon eluate was analyzed by protein A affinity HPLC.

Figure 19:
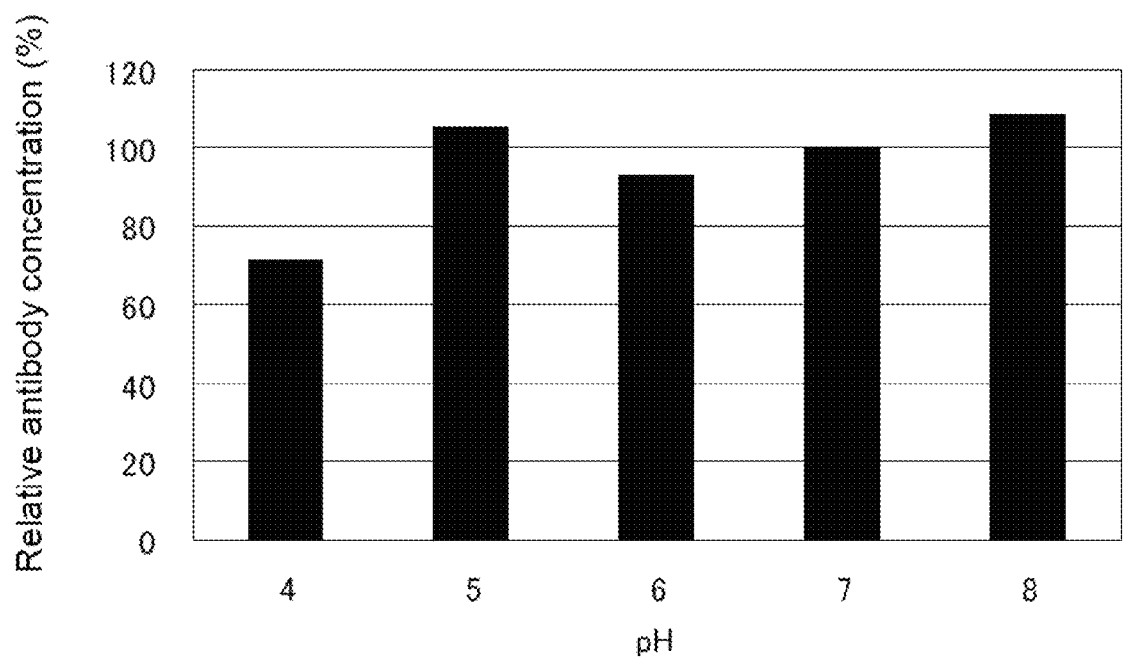
FIG. 19 shows the relative antibody concentration of activated carbon eluate at each pH by treatment of Mab B with activated carbon. The vertical axis represents the relative antibody concentration of activated carbon eluate (%), when the antibody concentration of activated carbon eluate at pH 7 is regarded as 100. From left, the relative antibody concentrations of activated carbon eluate at pH 4, pH 5, pH 6, pH 7, and pH 8 are represented.

When the antibody concentration of the activated carbon eluate at pH 7 was regarded as 100, the relative antibody concentration (%) at each pH was shown in FIG. 19. The antibody concentration at pH 4 was lower than that at other pH, and was approximately 70% of the antibody concentration at pH 7. At other pH, the antibody concentrations were within the range of ±10% of the antibody concentration at pH 7. With respect to the activated carbon treatment, the relative antibody concentrations and the antibody recovery rates at pH 5, pH 6, pH 7 and pH 8 were higher than those at pH 4.

The results of reduction rates of host cell proteins and relative antibody concentrations at each pH suggested that it is possible to perform the activated carbon treatment at any pH of pH 4 to 8, and preferably pH 4 to 6.

Example 14: Effect of Activated Carbon Raw Material in Activated Carbon Purification The CHO cell culture supernatant containing monoclonal antibodies (Mab B) clarified by microfiltration was adjusted to pH 4.6 with acetic acid. The formed precipitates were removed by centrifugation and filtration using a filter to obtain a clarified solution B.

Subsequently, each of the activated carbons listed in Table 1 was added to approximately 10 mL of the resulting clarified solution B, and mixed. Then, the mixtures were subjected to centrifugation and filtration using a filter to obtain activated carbon eluates.

TABLE 1

List of activated carbon evaluated

| Name | Raw material | Manufacturer |
| --- | --- | --- |
| SHIRASAGI P | Wood | Japan EnviroChemicals, Ltd. |
| SHIRASAGI DO-2 | Coconut-shell | Japan EnviroChemicals, Ltd. |
| SHIRASAGI DO-5 | Coal | Japan EnviroChemicals, Ltd. |

The contents of the polymers and the degradation products and the contents of host cell proteins in each of the activated carbon eluates were analyzed by gel filtration HPLC and by ELISA, respectively.

Figure 20:
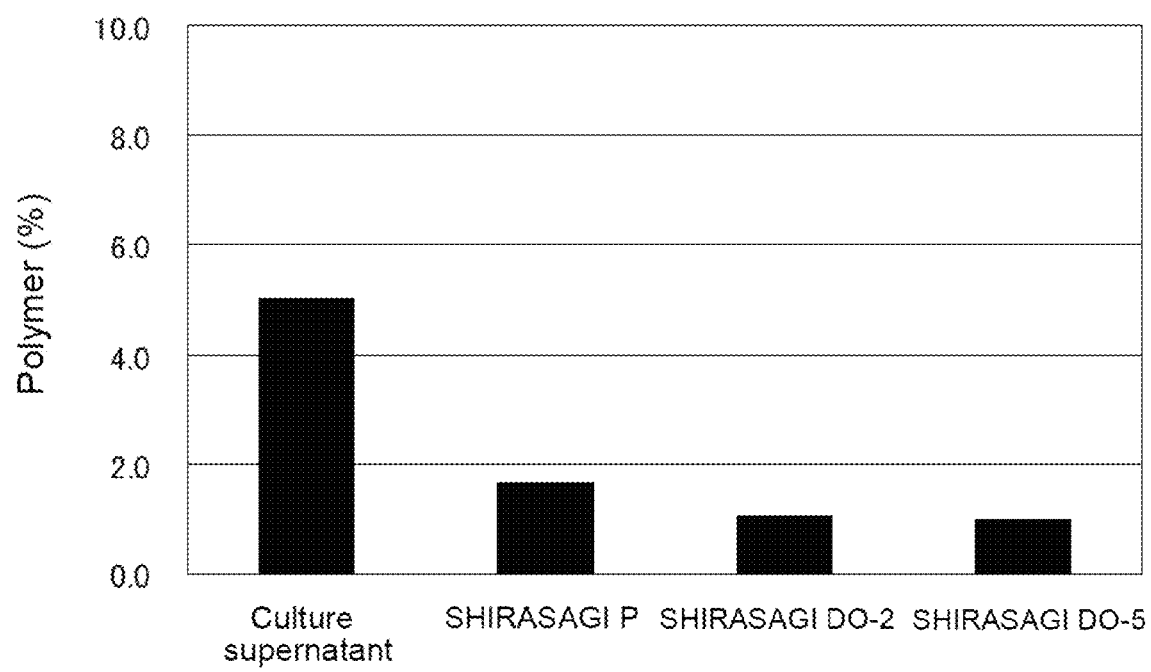
FIG. 20 shows the polymer content of activated carbon eluate by treatment of Mab B with different types of activated carbon. The vertical axis represents the polymer content of activated carbon eluate (%). From left, the polymer contents of activated carbon eluates in the culture supernatant, SHIRASAGI P, SHIRASAGI DO-2, and SHIRASAGI DO-5 are represented.
Figure 21:
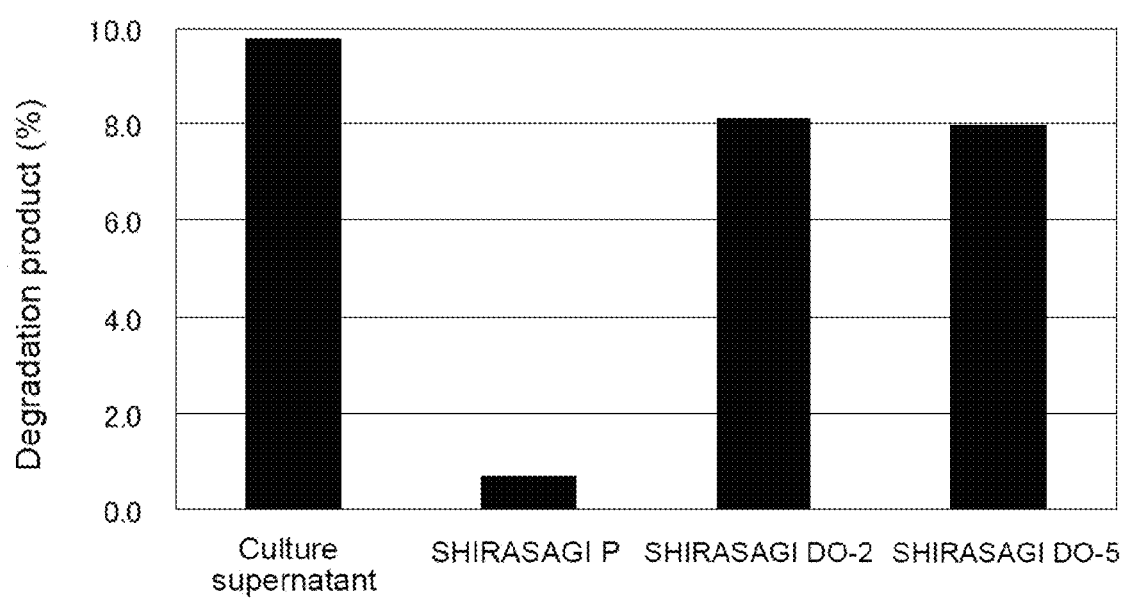
FIG. 21 shows the degradation product content of activated carbon eluate by treatment of Mab B with different types of activated carbon. The vertical axis represents the degradation product content of activated carbon eluate (%). From left, the degradation product contents of activated carbon eluates in the culture supernatant, SHIRASAGI P, SHIRASAGI DO-2, and SHIRASAGI DO-5 are represented.
Figure 22:
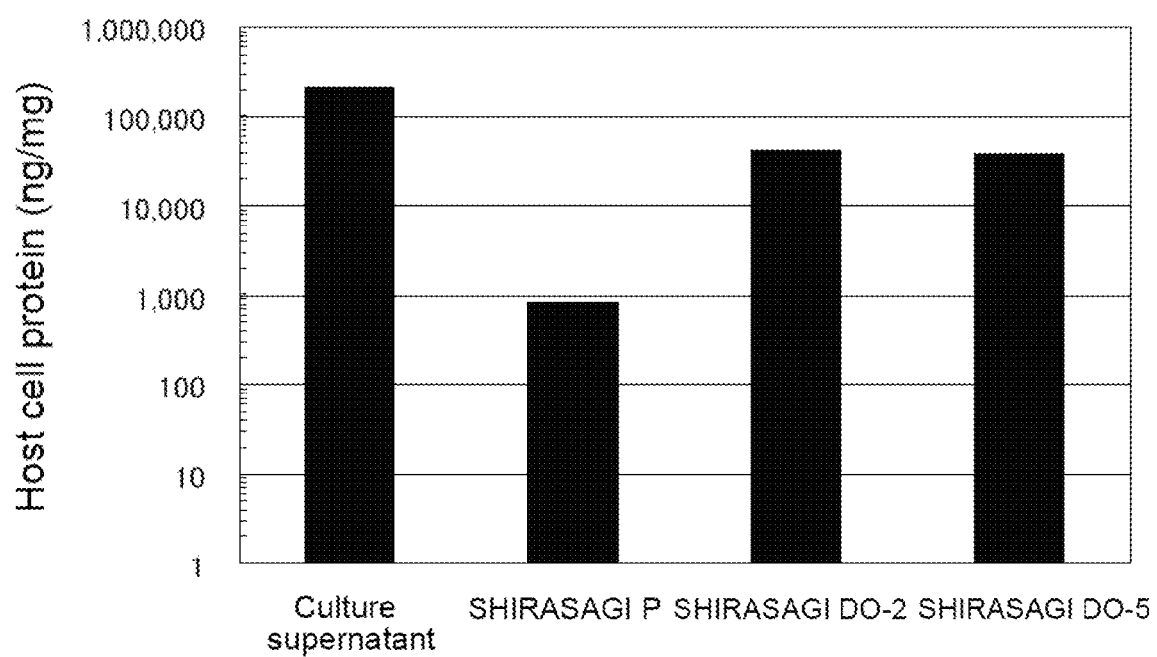
FIG. 22 shows the host cell protein content of activated carbon eluate by treatment of Mab B with different types of activated carbon. The vertical axis represents the host cell protein content of activated carbon eluate (ng/mg). From left, the host cell protein contents of activated carbon eluates in the culture supernatant, SHIRASAGI P, SHIRASAGI DO-2, and SHIRASAGI DO-5 are represented.

The analysis results of each activated carbon eluate were shown in FIGS. 20, 21, and 22. All of the activated carbon eluates obtained by SHIRASAGI P, SHIRASAGI DO-2 and SHIRASAGI DO-5 showed lower contents of polymers, degradation products, and host cell proteins than the culture supernatant. In particular, the activated carbon eluate obtained by using SHIRASAGI P, of which raw material is wood, showed much lower contents of degradation products and host cell proteins than other activated carbons.

Comparative Example 1: Mab A Purification (Purification Comprising Protein A Affinity Chromatography)

The clarified solution A obtained in Example 7 was adjusted to pH 6.4 with the Tris solution. Approximately 60 mL of this solution was applied to the protein A affinity chromatography column (manufactured by GE Healthcare Ltd., Inc., MabSelect SuRe, 5 mm ID×20 cm) that was equilibrated with the equilibration buffer consisting of 10 mmol/L Tris buffer (pH 7.0). After completion of the application, the column was washed with 5 column volumes of 10 mmol/L Tris buffer (pH 7.0) containing 1 mol/L sodium chloride and the equilibration buffer. Next, elution was carried out using 5 column volumes of 100 mmol/L glycine buffer (pH 3.2). The column-eluted fraction was pooled as a MabSelect SuRe eluate.

The resulting MabSelect SuRe eluate was adjusted to pH 8.0 with the Tris solution. This solution was applied to the anion exchange chromatography column (manufactured by GE Healthcare Ltd., Inc., Q Sepharose, 5 mm ID×20 cm) that was equilibrated with the equilibration buffer consisting of 10 mmol/L Tris buffer (pH 8.0). After completion of the application, 5 column volumes of equilibration buffer were passed through the column. The column non-adsorbed fraction was pooled as a Q Sepharose eluate.

The resulting Q Sepharose eluate was adjusted to pH 5.0 with the acetic acid solution. This solution was applied to the cation exchange chromatography column (manufactured by Applied Biosystems, POROS XS, 5 mm ID×20 cm) that was equilibrated with the equilibration buffer consisting of 10 mmol/L acetic acid buffer (pH 5.0). After completion of the application, 5 column volumes of equilibration buffer were passed through the column. Next, elution was carried out with a salt concentration gradient (10-column volumes) of gradually increasing the salt concentration in the 10 mmol/L acetic acid buffer (pH 5.0) containing 0.3 mol/L sodium chloride. A part of the column-eluted fraction was pooled as a POROS XS eluate. The POROS XS eluate was used as a final Mab A purified product.

Comparative Example 2: Mab B Purification (Purification Comprising Protein A Affinity Chromatography)

The clarified solution B obtained in Example 8 was adjusted to pH 6.4 with the Tris solution. Approximately 60 mL of this solution was applied to the protein A affinity chromatography column (manufactured by GE Healthcare Ltd., Inc., MabSelect SuRe, 5 mm ID×20 cm) that was equilibrated with the equilibration buffer consisting of 10 mmol/L Tris buffer (pH 7.0). After completion of the application, the column was washed with 5 column volumes of 10 mmol/L Tris buffer (pH 7.0) containing 1 mol/L sodium chloride and the equilibration buffer. Next, elution was carried out using 5 column volumes of 100 mmol/L glycine buffer (pH 3.2). The column-eluted fraction was pooled as a MabSelect SuRe eluate.

The resulting MabSelect SuRe eluate was adjusted to pH 8.0 with the Tris solution. This solution was applied to the anion exchange chromatography column (manufactured by GE Healthcare Ltd., Inc., Q Sepharose, 5 mm ID×20 cm)

that was equilibrated with the equilibration buffer consisting of 10 mmol/L Tris buffer (pH 8.0). After completion of the application, 5 column volumes of equilibration buffer were passed through the column. The column non-adsorbed fraction was pooled as a Q Sepharose eluate.

The resulting Q Sepharose eluate was adjusted to pH 5.0 with the acetic acid solution. This solution was applied to the cation exchange chromatography column (manufactured by Applied Biosystems, POROS XS, 5 mm ID×20 cm) that was equilibrated with the equilibration buffer consisting of 10 mmol/L acetic acid buffer (pH 5.0). After completion of the application, 5 column volumes of equilibration buffer were passed through the column. Next, elution was carried out with a salt concentration gradient (10-column volumes) of gradually increasing the salt concentration in the 10 mmol/L acetic acid buffer (pH 5.0) containing 0.3 mol/L sodium chloride. A part of the column-eluted fraction was pooled as a POROS XS eluate. The POROS XS eluate was used as a final Mab B purified product.

Although the present invention has been described in detail with reference to the specific embodiments, it will be apparent to those skilled in the art that various modifications and changes may be made thereto without departing from the scope and spirit of the invention.

The invention claimed is:

1. A method for purifying a monoclonal antibody from a sample comprising the monoclonal antibody and impurities, comprising
   (a) subjecting the sample to a precipitation step to form a precipitate and a supernatant, wherein said precipitation does not comprise a chromatography and said precipitation is carried out under an acid condition of pH 3 to 6;
   (b) contacting the resulting supernatant of the precipitation step (a) with an activated carbon to provide a non-adsorbed eluate, said activated carbon being unmodified; and
   (c) subjecting the non-adsorbed eluate from the contacting step (b) to separation of the monoclonal antibody from the impurities to obtain a purified monoclonal antibody,
   wherein the contacting step (b) is carried out at pH 4 to 6,
   wherein the impurities comprise host cell proteins, protein-derived polymers, protein-derived degradation products, and DNAs, and
   wherein the method does not comprise Protein A chromatography.

2. The purification method according to claim 1, wherein the monoclonal antibody has a molecular weight of 30000 or more.

3. The purification method according to claim 1, wherein the monoclonal antibody is selected from the group consisting of mouse antibodies, llama antibodies, chimeric antibodies, humanized antibodies, human antibodies, and antibodies with a modified Fc region.

4. The purification method according to claim 1, wherein the contacting step (b) is carried out under conditions where the impurities are adsorbed to the activated carbon and the monoclonal antibody is not adsorbed to the activated carbon.

5. The purification method according to claim 1, wherein the contacting step (b) is carried out at pH 4 to 5.

6. The purification method according to claim 1, wherein the activated carbon is an activated carbon from wood.

7. The purification method according to claim 1, wherein the activated carbon has an average micropore diameter of 0.5 to 5 nm.

8. The purification method according to claim 1, wherein the sample is selected from the group consisting of a plasma, serum, breast milk, or urine of a transgenic non-human host animal containing a gene coding for the monoclonal antibody; and a culture broth of a host cell which produces the monoclonal antibody, and
   wherein the purified monoclonal antibody contains 100,000 ng or less of host cell proteins per 1 mg of the purified monoclonal antibody.

9. The purification method according to claim 1, wherein the purified monoclonal antibody contains 10% or less of degradation products of the monoclonal antibody based on the total weight of the purified monoclonal antibody.

10. The purification method according to claim 1, wherein the purified monoclonal antibody contains 1000 ng or less of host cell proteins, 3% or less of protein-derived polymers, 3% or less of protein-derived degradation products, and 10 pg or less of DNAs, per 1 mg of the purified monoclonal antibody.

11. A method for preparing a purified monoclonal antibody, comprising
   (a) producing the monoclonal antibody in a host cell or in a culture broth containing the host cell under conditions where the monoclonal antibody is produced;
   (b) providing a sample containing the host cell or the culture broth, said sample containing the monoclonal antibody and impurities;
   (c) subjecting the sample to a pre-treatment comprising a precipitation and a precipitate removal to give a pre-treated sample, wherein said pre-treatment does not comprise a chromatography and the precipitation is carried out under an acidic condition of pH 3 to 6;
   (d) contacting the pre-treated sample obtained in (c) with an activated carbon, said activated carbon being unmodified, wherein the impurities are adsorbed to the activated carbon; and
   (e) recovering the non-adsorbed monoclonal antibody from the impurities adsorbed to the activated carbon to provide the purified monoclonal antibody,
   wherein the (d) contacting the pre-treated sample with an activated carbon is carried out at pH 4 to 6,
   wherein the impurities comprise host cell proteins, protein-derived polymers, protein-derived degradation products, and DNAs, and
   wherein the method does not comprise Protein A chromatography.

12. The preparation method according to claim 11, further comprising any one of anion exchange chromatography, cation exchange chromatography, hydrophobic interaction chromatography, or multimodal chromatography, wherein said chromatography is performed after the activated carbon treatment of step (d).

13. The preparation method according to claim 12, wherein at least one of the anion exchange chromatography, cation exchange chromatography, hydrophobic interaction chromatography, or multimodal chromatography is an adsorption-mode chromatography.

14. The preparation method according to claim 11, wherein the purified monoclonal antibody contains 100 ng or less of host cell proteins per 1 mg of the purified monoclonal antibody.

15. The preparation method according to claim 11, wherein the purified monoclonal antibody contains 3.5% or less of degradation products of the monoclonal antibody based on the total weight of the purified monoclonal antibody.

16. The preparation method according to claim 11, wherein the purified monoclonal antibody contains 1000 ng or less of host cell proteins, 3% or less of protein-derived polymers, 3% or less of protein-derived degradation products, and 10 pg or less of DNAs, per 1 mg of the purified monoclonal antibody.

\* \* \* \* \*